(12) United States Patent
Porgador

(10) Patent No.: US 9,399,667 B2
(45) Date of Patent: Jul. 26, 2016

(54) PEPTIDES DERIVED FROM CYTOTOXICITY RECEPTOR NATURAL KILLER PROTEIN 44 NKP44

(71) Applicant: 03;B. G. NEGEV TECHNOLOGIES AND APPLICATIONS LTD., AT BEN-GURION UNIVERSITY, Beer-Sheva (IL)

(72) Inventor: Angel Porgador, Lehavim (IL)

(73) Assignee: B. G. NEGEV TECHNOLOGIES AND APPLICATIONS LTD., AT BEN-GURION UNIVERSITY, Beer-Sheva (IL)

( * ) Notice: Subject to any disclaimer, the term of this patent is extended or adjusted under 35 U.S.C. 154(b) by 0 days.

(21) Appl. No.: 14/492,713

(22) Filed: Sep. 22, 2014

(65) Prior Publication Data

US 2015/0105334 A1  Apr. 16, 2015

Related U.S. Application Data

(63) Continuation-in-part of application No. PCT/IL2013/050235, filed on Mar. 14, 2013.

(60) Provisional application No. 61/613,504, filed on Mar. 21, 2012.

(51) Int. Cl.
| | | |
|---|---|---|
| A61K 38/00 | (2006.01) | |
| C07K 7/06 | (2006.01) | |
| C07K 7/08 | (2006.01) | |
| C07K 14/705 | (2006.01) | |

(52) U.S. Cl.
CPC ............... C07K 14/705 (2013.01); C07K 7/06 (2013.01); C07K 7/08 (2013.01); A61K 38/00 (2013.01)

(58) Field of Classification Search
CPC ........ A61K 38/00; C07K 14/705; C07K 7/06; C07K 7/08
USPC ........ 514/21.4, 21.5, 21.6; 530/326, 328, 350
See application file for complete search history.

(56) References Cited

U.S. PATENT DOCUMENTS

| | | | |
|---|---|---|---|
| 4,237,224 A | 12/1980 | Cohen et al. | |
| 4,273,875 A | 6/1981 | Manis | |
| 4,363,877 A | 12/1982 | Goodman | |
| 4,428,941 A | 1/1984 | Galibert | |
| 4,431,739 A | 2/1984 | Riggs | |
| 4,816,397 A | 3/1989 | Boss et al. | |
| 4,816,567 A | 3/1989 | Cabilly et al. | |
| 4,946,778 A | 8/1990 | Ladner et al. | |
| 5,595,756 A * | 1/1997 | Bally ................. | A61K 9/1272 264/4.1 |
| 5,693,762 A | 12/1997 | Queen et al. | |
| 5,712,120 A | 1/1998 | Rodriguez et al. | |
| 5,969,108 A | 10/1999 | McCafferty et al. | |

| | | |
|---|---|---|
| 2004/0038339 A1 | 2/2004 | Kufer et al. |
| 2007/0203054 A1 | 8/2007 | Mandelboim |
| 2007/0231813 A1 | 10/2007 | Cartron et al. |
| 2008/0274047 A1 | 11/2008 | Romagne et al. |
| 2012/0076753 A1 | 3/2012 | Mandelboim et al. |

FOREIGN PATENT DOCUMENTS

| | | |
|---|---|---|
| WO | 9117271 A1 | 11/1991 |
| WO | 9201047 A1 | 1/1992 |
| WO | 0208287 A2 | 1/2002 |
| WO | 02/072631 A2 | 9/2002 |
| WO | 2004053054 A2 | 6/2004 |
| WO | 2005000086 A2 | 1/2005 |
| WO | 2005051973 A2 | 6/2005 |
| WO | 2007/048849 | 5/2007 |
| WO | 2009148568 A1 | 12/2009 |
| WO | 2010106542 A2 | 9/2010 |
| WO | 2013/140393 A1 | 9/2013 |

OTHER PUBLICATIONS

Water is natural product from http://www.biology-online.org/dictionary/Water, pp. 1-3. Accessed Apr. 24, 2014.*
Neidle Stephen Ed., Cancer Drug Design and Discovery, 2008, 427-431.*
Gura, Trisha, "Systems for identifying new drugs are often faulty," Science, Nov. 7, 1997, 278: 1041-1042.*
Auberbach R, Akhtar N, Lewis RL, Shinners BL, "Angiogenesis assays: Problems and pitfalls," Cancer and Metatasis Reviews, 2000, 19: 167-172.*
Jain, RK, "Barriers to Drug Discovery in Solid Tumors," Scientific American, Jul. 1994, 58-65.*
Sporn MB, Suh N, "Chemoprevention of cancer," Carcinogenesis, 2000, 21(3): 525-530.*
GenBank Accession No. NP_004819, pp. 1-4. Accessesd May 9, 2016.*
GenBank Accession No. NP_001181874, pp. 1-2. Accessed May 9, 2016.*
GenBank Accession No. NP_001186438, pp. 1-4. Accessed May 9, 2016.*
Genbank Accession No. NP_001186439, pp. 1-4. Accessed May 9, 2016.*
GenBank Accessed No. O95944, pp. 1-6. Accessed May 12, 2016.*
Aktas et al, "Relationship between CD107a expression and cytotoxic activity". Cell Immunology 254:2:149-54 (2009).
A. Alba et al, "IFN beta Accelerates Autoimmune Type 1 Diabetes in Nonobese Diabetic Mice and Breaks the Tolerance to beta Cells in Nondiabetes-Prone Mice". The Journal of Immunology 173:11: 6667-6675 (2004).
A. Alba et al, "Natural killer cells are required for accelerated type 1 diabetes driven by interferon-beta" Clinical and Experimental Immunologyy 151:3:467-75 (2008).

(Continued)

*Primary Examiner* — Julie Ha
(74) *Attorney, Agent, or Firm* — Browdy and Neimark, PLLC

(57) ABSTRACT

Specific peptides derived from the cytotoxicity receptor natural killer protein 44 (NKp44) useful for treating diseases such as cancer are described. The invention further relates to compositions comprising a fragment of the extracellular region of NKp44 for preventing or treating cancer.

14 Claims, 13 Drawing Sheets

(56) References Cited

OTHER PUBLICATIONS

Galit Alter et al, "CD107a as a functional marker for the identification of natural killer cell activity" Journal Immunology Methods 294:1-2:15-22 (2004).

Stephen F. Altschul et al., "Basic Local Alignment Search Tool". J Mol Biol 215: 3: 403-410 (1990).

Stephen F. Alschul et al, "Gapped BLAST and PSI-BLAST: a new generation of protein database search programs" Nucleic Acids Research 25:17: 3389-402 (Jul. 1997).

Tal I Arnon et al., "Recognition of viral hemagglutinins by NKp44 but not by NKp30". Eur J Immunol 31:9: 2680-2689 (2001).

Tal I Arnon et al., "The mechanisms controlling the recognition of tumor- and virus-infected cells by NKp46". Blood. 103:2 : 664-672 (Jan. 2004).

Roberto Biassoni et al, "The murine homologue of the human NKp46, a triggering receptor involved in the induction of natural cytotoxicity". Eur J Immunol 29:3: 1014-1020 (1999).

Surendra Chaturvedi et al, "Stabilization of triple-stranded oligonucleotide complexes: use of probes containing alternating phosphodiester and stereo-uniform cationic phosphoramidate linkages". Nucleic Acids Research 24:12: 2318-2323 (1996).

Tim Clackson et al, "Making antibody fragments using phage display libraries". Nature 352:6336: 624-628 (Aug. 1991).

Paul C. Driscoll et al., "Two-dimensional Nuclear Magnetic Resonance Analysis of a Labeled Peptide bound to a class II Major Histocompatibility Complex Molecule". J Mol Biol 232:2: 342-350 (1993).

Malin Flodstrom et al, "Reduced Sensitivity of Inducible Nitric Oxide Synthase-Deficient Mice to multiple low-dose streptozotocin-Induced Diabetes". Diabetes 48:4:706-13 (Apr. 1999).

A. K. Foulis et al, "A search for evidence of viral infection in pancreases of newly diagnosed patients with IDDM". Diabetologia 40:1: 53-61 (1997).

Chamutal Gur et al, "The activating receptor NKp46 is essential for the development of type 1 diabetes". Nature Immunology 11:2 : 121-8 (Feb. 2010).

Werner Gurr et al, "RegII is a beta-cell protein and autoantigen in diabetes of NOD mice". Diabetes 56:1: 34-40 (Jan. 2007).

Gili G Halfteck et al, "Enhanced in Vivo Growth of Lymphoma Tumors in the Absence of the NK-Activating Receptor NKp46/NCR1". The Journal of Immunology 182:4: 2221-2230 (2009).

Marc S. Horwitz et al, Diabetes induced by Coxsackie virus: Initiation by bystander damage and not molecular mimicry. Nature Medicine 4:7: 781-785 (Jul. 1998).

William D. Huse et al, "Generation of a Large Combinatorial Library of the Immunoglobulin Repertoire in Phage Lambda" Science 246:4935: 1275-1281 (Dec. 1989).

Michal Jaron-Mendelson et al, "Dimerization of NKp46 Receptor is Essential for NKp46-Mediated Lysis: Characterization of the Dimerization Site by Epitope Aapping". The Journal of Immunology 188:12: 6165-6174 (2012).

Peter T. Jones et al, "Replacing the complementarity-determining regions in a human antibody with those from a mouse". Nature. 321:6069: 522-525 (May 1986).

Samuel Karlin et al "Applications and statistics for multiple high-scoring segments in molecular sequences". Proc Natl Acad Sci U S A. 90:12: 5873-5877 (Jun. 1993).

Yoshihiro Kitagawa et al, "Islet Cells but not Thyrocytes are Susceptible to Lysis by NK Cells". Journal Autoimmunity 4:5: 703-716 (Jun. 1991).

G. Kohler et al, "Continuous cultures of fused cells secreting antibody of predefined specificity". Nature 256:5517: 495-497 (Aug. 1975).

Lewis L. Lanier "NK Cell Recognition". Annu. Rev. Immunol. 23: 225-274 (2005).

BM Lodde et al., "NOD mouse model for Sjogren's syndrome: lack of longitudinal stability". Oral Diseases 12:6: 566-572 (2006).

Melissa Lodoen et al, "NKG2D-mediated Natural Killer Cell Protection Against Cytomegalovirus Is Impaired by Viral gp40 Modulation of Retinoic Acid Early Inducible 1 Gene Molecules". The Journal of Experimental Medicine 197:10: 1245-53 (May 2003).

Peter Mackay et al, "Spontaneous diabetes mellitus in the Bio-Breeding/Worcester rat. Evidence in vitro for natural killer cell lysis of islet cells". J Clin Invest 77:3: 916-24 (Mar. 1986).

Ofer Mandelbolm et al. "Recognition of haemagglutinins on virus-infected cells by NKp46 activates lysis by human NK cells". Nature 409:6823: 1055-1060 (Feb. 2001).

James D. Marks et al., "By-passing immunization. Human antibodies from V-gene libraries displayed on phage". J Mol Biol 222:3: 581-597 (Sep. 1991).

Shirou Matsumoto et al., "Isolation of tissue progenitor cells from duct-ligated salivary glands of swine". Cloning Stem Cells 9:2: 176-90 (2007).

M. D. Matteucci et al "Synthesis of deoxyoligonucleotides on a polymer support". J Am Chem Soc 103:11: 3185-3191 (1981).

Jennifer Mayfield et al "Diagnosis and classification of diabetes mellitus: new criteria". Am Family Physician 58:6: 1355-1362, 1369-1370 (Oct. 1998).

Bruce Merrifield "Solid phase synthesis" Science 232:4748: 341-347 (Apr. 1986).

Jun-Ichi Miyazaki et al, "Establishment of a pancreatic beta cell line that retains glucose-inducible insulin secretion: special reference to expression of glucose transporter isoforms" Endocrinology 127:1 : 126-32 (1990).

Maho Niwa et al, "A role for presenilin-1 in nuclear accumulation of Ire1 fragments and induction of the mammalian unfolded protein response". Cell 99:7: 691-702 (Dec. 1999).

Suzanne Peyrottes et al., "Oligodeoxynucleoside phosphoramidates (P-NH2): synthesis and thermal stability of duplexes with DNA and RNA targets" Nucleic Acids Research. 24:10: 1841-1848 (Apr. 1996).

Laurent Poirot et al "Natural killer cells distinguish innocuous and destructive forms of pancreatic islet autoimmunity". Proc Natl Acad Sci U S A. 101:21: 8102-8107 (May 2004).

Leonard G. Presta "Antibody engineering". Current Opinion in Structural Biology 2:4: 593-596 (1992).

David H. Raulet, "Roles of the NKG2D Immunoreceptor and Its Ligands". Nature Review Immunology. 3:10: 781-790 (Oct. 2003).

Lutz Riechmann et al "Reshaping human antibodies for therapy". Nature 332:6162: 323-327 (Mar. 1988).

M. R. Suresh et al, "Bispecific monoclonal antibodies from hybrid hybridomas". Methods in Enzymology. 121: 210-228 (1986).

James P. Tam et al., "An SN2 Deprotection of Synthetic Peptides with a low Concentration of HF in Dimethyl Sulfide: Evidence and Application in Peptide Synthesis". J Am Chem Soc. 105:21: 6442-6455 (1983).

World Health Organization "Definition and diagnosis of diabetes mellitus and intermediate hyperglycemia" International Diabetes Federation. Geneva, Switzerland (2006).

* cited by examiner 1 2 3 4 5 6 7
YDTPT LSVHP GPEVI SQEKV$_1$ TFYCR$_2$ LDTAT$_3$ SMFLL$_4$ 8 9 10 11 12 13
LKEGR$_5$ SSHVQ$_6$ RGYGK$_7$ VQAEF$_8$ PLGPV$_9$ TTAHR$_{10}$ 14 15 16 17 18 19
GTYRC$_{11}$ FGSYN$_{12}$ NHAWS$_{13}$ FPSEP$_{14}$ VKLLV$_{15}$ TGDIE$_{16}$ 20 21 22 23 24
NTSLA$_{17}$ PEDPT$_{18}$ FPADT$_{19}$ WGTYL$_{20}$ LTTET$_{21}$GLQKD$_{22}$

HALWD$_{23}$HTAQ$_{24}$

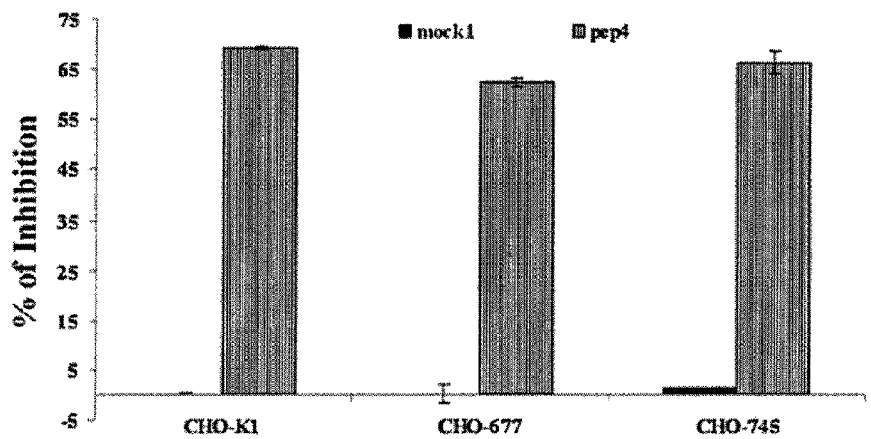
Figure 11A
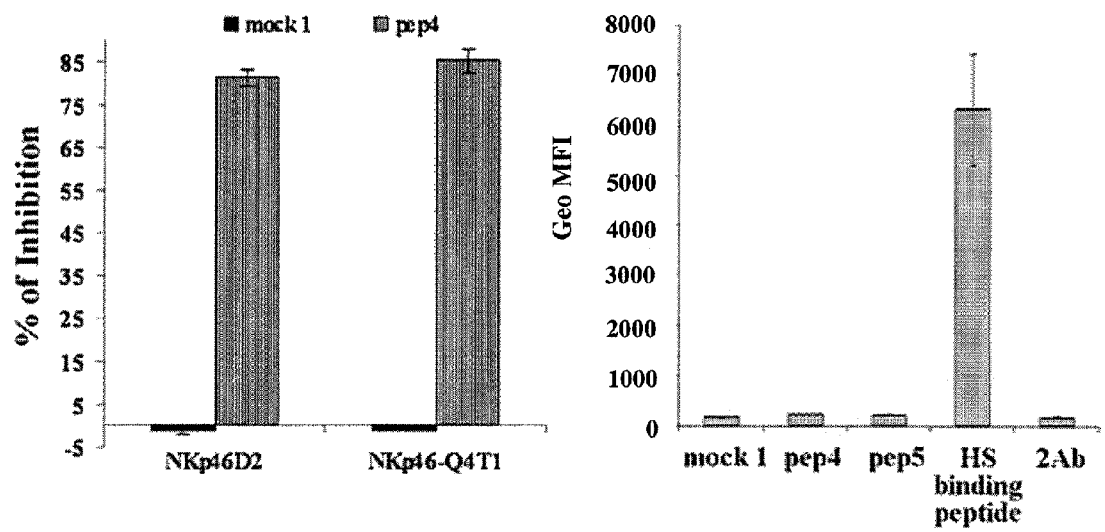
Figure 11B
Figure 11C

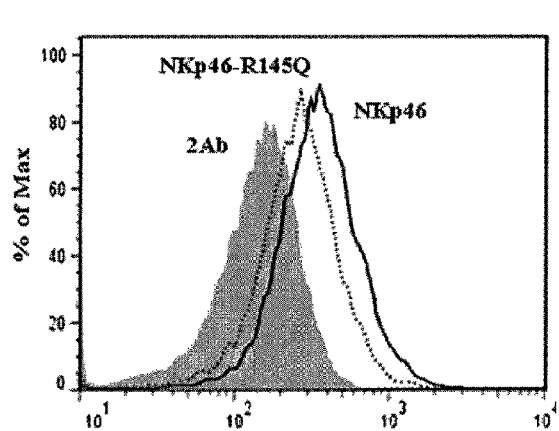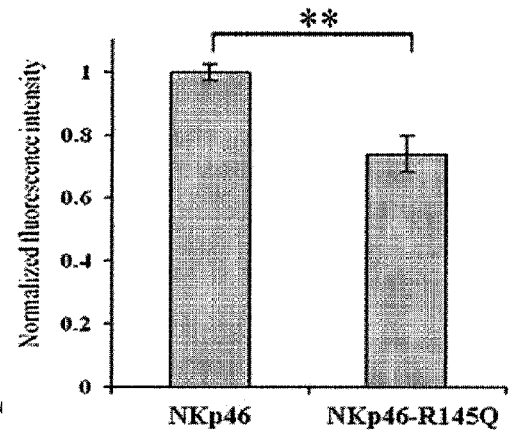
Figure 13A
Figure 13B
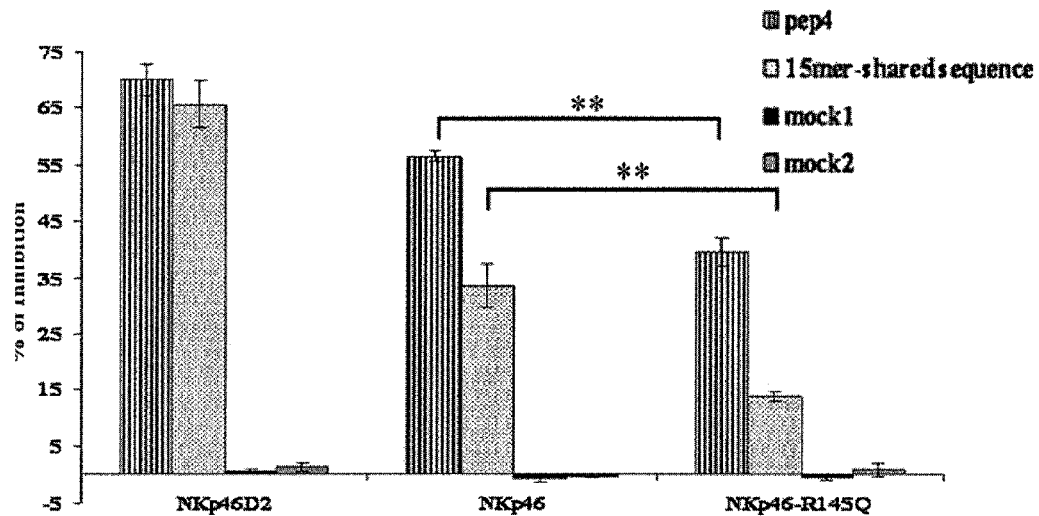
Figure 13C

US 9,399,667 B2

PEPTIDES DERIVED FROM CYTOTOXICITY RECEPTOR NATURAL KILLER PROTEIN 44 NKP44

CROSS REFERENCE TO RELATED APPLICATIONS

The present application is a continuation-in-part of International Application Number PCT/IL2013/050235 filed 14 Mar. 2013, which claims the benefit of Provisional application No. 61/613,504 filed 21 Mar. 2012, both of which are hereby incorporated by reference in their entirety as if fully set forth herein.

FIELD OF THE INVENTION

The present invention relates to peptide fragments derived from the extracellular region of NKp44 and NKp46 receptor expressed on natural killer (NK) cells. In particular, the present invention identifies specific peptides that inhibit the binding of the parental NK receptor domains to pancreatic beta cells or affect the binding to cancer cells.

BACKGROUND OF THE INVENTION

Natural killer (NK) cells are bone marrow derived lymphocytes that constitute a key frontline defense against a range of hazardous conditions including viral infection and tumor transformation. Although NK cells can kill target cells spontaneously without prior stimulation, a delicate balance between inhibitory and activating signals tightly regulates their activation. NK cells express a family of inhibitory and activating receptors that recognize major histocompatibility complex (MHC) class I molecules. Engagement of these receptors results in the transduction of inhibitory signals that, under normal physiological conditions, predominate over those mediated via activating receptors. This insures that healthy cells, expressing adequate amounts of MHC class I, will be protected from NK cells attack, while cells that have lost normal expression of MHC class I molecules, often resulting from viral infection or cell transformation, will be destroyed.

NK cells play a crucial role in the initial defense against virus-infected cells and cancer cells. They interact with antigen presenting cells (APCs), serve as APCs, directly kill hazardous cells and further secrete chemokines and immunomodulatory cytokines such as IFN-γ and TNF-α, which cause T cells to shift into a Th1 phenotype. NK cells have been identified in target organs of patients suffering from autoimmune diseases and they are capable of attacking autologous cells.

The killing mediated by NK cells involves several activating receptors, such as the natural cytotoxicity receptors (NCRs) NKp30, NKp44 and NKp46, and NKG2D. NKp46 and NKp30 are present exclusively on NK cells, whether resting or activated, while NKp44 is expressed specifically on activated NK cells. NKp46 is considered to be the most specific NK marker for which an ortholog protein (NCR-1) has been found in mice. The NCRs belong to the Ig superfamily but share no homology with each other and only a low degree of identity with any known human molecules. All of these NCRs are capable of mediating direct killing of tumor and virus-infected cells and are specific for non-MHC ligands.

Upon engagement, NCRs transduce activating signals through the association with various adaptor molecules (including the DAP12 and zeta chain proteins) that carry immunoreceptor tyrosine-based activation motifs (ITAM) in their cytoplasmatic tail, allowing activation via the src-kinase and syc-signaling pathway.

Type 1 diabetes (T1D; also known as type 1 diabetes mellitus and immune-mediated diabetes) is a multifactorial autoimmune disease in which insulin-producing beta cells in pancreatic islets are destroyed by autoreactive T cells. Mononuclear cells infiltrate the pancreatic islets of Langerhans during a variable period of clinically silent inflammation (insulitis), and eventually T cells destroy insulin-producing beta cells. Full-blown type 1 diabetes ensues when most beta cells are destroyed and the pancreas ceases to produce enough insulin. Exogenous insulin must then be administered for life. Weeks or months after insulin treatment starts, patients with type 1 diabetes can experience a variable period of remission, which is thought to result from restored insulin production by residual beta cells. Continued treatment with exogenous insulin is needed to preserve the residual beta cells, which can still naturally modulate glucose metabolism.

Type 2 diabetes is characterized by insulin resistance which may be combined with reduced insulin secretion. The defective responsiveness to insulin is believed to involve the insulin receptor. In the early stage of type 2 diabetes, hyperglycemia can be reversed by a variety of measures and medications that improve insulin sensitivity or reduce glucose production by the liver. As the disease progresses, impairment of insulin secretion occurs, and therapeutic replacement of insulin is often required. Beta cell destruction also occurs in type 2 diabetes, and it has been proposed that one contributing factor is increased beta cell apoptosis.

A widely used model of autoimmune T1D is the non-obese diabetic (NOD) mouse, which develops diabetes spontaneously after a variable period of insulitis, similarly to human T1D. NOD mice demonstrate insulitis from 4-5 weeks of age, and after a variable period of chronic inflammation, diabetes develops about 10-20 weeks later, with most females diabetic by 30 weeks of age. An additional accepted model of experimental autoimmune diabetes in mice is the induction of diabetes by multiple injections of low doses of streptozotocin (LDST). Streptozotocin causes diabetes by direct beta cell cytotoxicity, as well as by initiation of cell mediated autoimmune reaction against beta cells. Adoptive transfer of activated splenocytes from LDST-treated mice has been disclosed to induce diabetes in untreated healthy mice.

T1D is considered to be a T cell mediated disease. However, several studies suggest that the innate immune system, in particular natural killer (NK) cells, play a role in the pathogenesis of the disease. For example, it has been disclosed that NK cells infiltrate the islets of NOD mice, and islet inflammation mediated mainly by NK cells has been reported in human T1D. Several alterations in NK cell compartments in patients with T1D have been disclosed, both at the onset of the disease and after long term hyperglycemia. Furthermore, the essential role of NK cells in diabetes development was demonstrated in murine models of accelerated T1D (Poirot et al., *Proc Natl Acad Sci USA* 101, 8102-8107 (2004)). Poirot et al., 2004 disclose that the proportion and number of NK cells, and the timing of their entry to the pancreas correlate with the severity of T1D in transgenic NOD mice. It has also been disclosed that depletion of NK cells in transgenic NOD mice models of accelerated T1D significantly inhibits diabetes development. However, the molecular mechanisms of NK cell involvement in T1D are still unknown.

Some of the inventors of the present invention have disclosed that soluble NKp46- and NKp44-immunoglobulin (Ig) fusion proteins, but not an NKp30-Ig fusion protein, specifically bind to hemagglutinin of influenza virus and to hemagglutinin-neuraminidase of Sendai virus (Mandelboim, et al. Nature 409, 1055-1060 (2001); Arnon et al. Eur J Immunol. 2001; 31:2680-2689; Arnon et al. Blood. 2004; 103:664-672). According to these disclosures, this interaction is functional and can mediate an enhanced killing of infected cells. Furthermore, the enhanced killing can be abolished by antibodies that block either the HA or the receptors NKp46 and NKp44.

The human NKp46 receptor has multiple isoforms including isoform a (GenBank Accession No. CAA04714); isoform b (GenBank Accession No. CAA06872); isoform c (GenBank Accession No. CAA06873), and isoform d (GenBank Accession No. CAA06874). In general the NKp46 receptor comprises two extracellular Ig-like domains of the C2 type, a transmembrane portion and an intracellular segment. The extracellular portion of NKp46 comprises a D1 domain, designated NKp46D1 (corresponding to residues 22-120 of the mature full length protein of isoform a), and a D2 domain, designated NKp46D2, comprising 134 amino acid residues (corresponding to residues 121-254 of the full length protein of isoform a).

PCT Application Publication No. WO 02/08287 of the present inventor and others discloses a targeting complex comprising a target recognition segment comprising one of NKp30, NKp44 and NKp46 or a functional fragment thereof; and an active segment comprising an active substance such as a cytotoxic moiety, an imaging moiety or an Ig fragment. According to the disclosure, fusion proteins containing the extracellular domains NKp30, NKp44 or NKp46 fused to the Fc portion of human IgG1 (termed respectively NKp30-Ig, NKp44-Ig and NKp46-Ig), bind certain tumor cell targets, and NKp46-Ig binds to virus infected cells. Further disclosed are fusion proteins containing either D1 or D2 fused to the Fc portion of human IgG1 (termed respectively NKp46D1-Ig and NKp46D2-Ig), and the observation that D2 is responsible for interaction with viral hemagglutinin.

PCT Application Publication No. WO 2004/053054 of the present inventor and others discloses that an NKp30-Ig conjugate is effective in inducing tumor regression in vivo in cancer bearing nude mice. Further disclosed are pharmaceutical compositions comprising a first segment selected from NKp30, NKp44 and NKp46 or a functional fragment thereof, and a second segment selected from an Ig molecule or a fragment or Fc fragment thereof, for eliminating a tumor or inhibiting growth of a tumor.

PCT Application Publication No. WO 2005/000086 of the present inventor and others discloses isolated peptide fragments comprising glycosylated residues derived from NKp44 and NKp46 that comprise epitopes essential for binding to target cells. According to the disclosure, a linker peptide within the D2 domain of NKp46 designated NKp46LP, which corresponds to residues 215-254 of the full length protein, contains an O-glycosylated threonine residue that is essential for the binding of NKp46 to viral infected cells and to tumor cells. Further disclosed is a linker peptide derived from the extracellular domain of NKp44 which corresponds to residues 136-190 of the full length protein and comprises a hyperglycosylated region comprising at least 14 predicted glycosylation sites that contribute to the efficient binding to viral-infected cells. Further disclosed are isolated peptide fragments of 10-100 amino acids, derived from the aforementioned peptides which retain the biological activity of interest.

PCT Application Publication No. WO 2005/051973 of the present inventor and others discloses peptides derived from NKp46, NKp44 and NKp30 which comprise sulfated polysaccharides and are capable of binding to tumor cells. Specifically disclosed are peptides derived from NKp46 corresponding to residues 153-172 and 153-175 of the full length protein; peptides derived from NKp30 corresponding to residues 57-84 and 57-76 of the full length protein, and a peptide derived from NKp44 corresponding to residues 51-74 of the full length protein U.S. Patent Application Publication No. 2008/0274047 discloses methods of treating immunoproliferative and autoimmune disorders using antibodies which bind NK cell receptors, particularly to deplete cells involved in the immunoproliferative pathology. According to the disclosure, immmunoproliferative disorders which may be treated by the invention include type 1 diabetes, and the antibody may be directed against human NKp46. Further disclosed is that injection of anti-human NKp46 antibodies into transgenic mice expressing human NKp46 resulted in depletion of NK cells in blood, spleen, liver and lung.

U.S. Patent Application Publication No. 2007/0231813 discloses methods and compositions to assess the therapeutic response of a subject to a therapeutic composition comprising an Fc portion, preferably a therapeutic antibody, wherein the therapeutic antibody preferably is not capable of, or is not required to be capable of, depleting target cells. According to the disclosure, the composition may specifically bind an NK receptor inter alia NKp46 and the subject may have juvenile onset diabetes.

U.S. Patent Application Publication No. 2004/0038339 discloses a multifunctional polypeptide comprising (a) a first domain comprising a binding site specifically recognizing an extracellular epitope of the NKG2D receptor complex; and (b) a second domain having receptor or ligand function, wherein said receptor or ligand function may be an antigen binding site of an antibody or fragment thereof directed against inter alia NKp46 which interacts with haemagglutinin (HA) of influenza virus. According to the disclosure, the composition may be used for treating autoimmune diseases, inter alia insulin-dependent diabetes mellitus, wherein elimination of the subpopulation of immune cells that causes the disease is desired.

PCT Application Publication No. WO 02/072631 discloses an MHC molecule construct comprising a carrier molecule having attached thereto one or more MHC molecules, and optionally further comprising one or more biologically active molecules inter alia NKp46. According to the disclosure, the construct may be used for prognosing or diagnosing a disease, or determining the effectiveness of a medicament against a disease, and the disease may be type 1 diabetes.

PCT Application Publication No. WO 2009/148568 discloses a cellular composition comprising at least about 30% human facilitating cells (hFCs) having a phenotype of CD8+/alpha beta TCR-/delta gamma TCR-/CD56$^{dim/neg}$, and wherein the hFCs optionally further have a phenotype including NKp46+. According to the disclosure, the composition may be used for transplantation into a human subject having a disease inter alia diabetes.

Gur et al., of the inventor of the present invention and others discloses that human NKp46 and its murine ortholog NCR-1 specifically recognize both human and murine pancreatic beta cells, and that NK cells degranulate upon interaction with murine beta cells in an NKp46-dependent manner. Further disclosed is that diabetes development is impaired in the absence of NKp46 and that the highest percentage of NK cells in the pancreas is observed at the time when insulitis develops into diabetes (the "pre-diabetic" stage). Furthermore, it is disclosed that injection of NKp46 fusion proteins to female NOD mice, either at the early stage of insulitis or at the late, pre-diabetic stage, almost entirely prevents diabetes development (Gur et al., Nat Immunol. 2010 February; 11(2):121-8).

U.S. Patent Application Publication No. 20120076753, of the inventor of the present invention and co-workers, relates to use of NKp46 for preventing and treating diabetes, and particularly to compositions comprising a fragment of the extracellular region of NKp46 for preventing the onset and progression of diabetes.

There remains an unmet need for small peptide molecules that can be used in therapeutic compositions and methods directed to prevention and treatment of serious diseases such as diabetes and cancer.

SUMMARY OF THE INVENTION

The present invention provides specific isolated peptides corresponding to fragments of the extracellular regions of the natural cytotoxicity receptor protein NKp44 and NKp46. In some embodiments, these peptides may be used in therapeutic compositions and methods directed to prevention and treatment of serious diseases, including, but not limited to diabetes or cancer.

In a first aspect, the invention provides an isolated peptide of about 10 to 30 amino acid residues in length which corresponds to a fragment of the ectodomain of NKp44, the peptide comprising the amino acid sequence selected from the group consisting of: SEQ ID NOS: 25-44. In another particular embodiment, the NKp44 is a human natural cytotoxicity receptor protein. In a particular embodiment, the human NKp44 is an isoform selected from the group consisting of isoform 1, isoform 2, and isoform 3.

In some embodiments, the peptide comprises the amino acid sequence as set forth in SEQ ID NO: 31, SEQ ID NO: 32, SEQ ID NO: 33 or SEQ ID NO: 34. In some embodiments, the peptide consists of an amino acid sequence selected from the group consisting of: SEQ ID NOS: 31, 32, 33 and 34.

In yet another aspect, the invention provides an isolated peptide of about 10 to 30 amino acid residues in length which corresponds to a fragment of the ectodomain of NKp44, the isolated peptide comprising an amino acid sequence selected from the group consisting of SEQ ID NO: 59 (VCIRLVTSSK) and SEQ ID NO: 60 (VTSSKPRTXA), wherein X in SEQ ID NO: 60 denotes any hydrophobic amino acid. In certain embodiments, the X in SEQ ID NO: 60 denotes V or M. Each possibility represents a separate embodiment of the invention.

In another embodiment, the peptide comprises the amino acid sequence set forth in SEQ ID NO: 61 (VCIRLVTSSKPRTXA), wherein X in SEQ ID NO: 61 denotes any hydrophobic amino acid. In certain embodiments, the X in SEQ ID NO: 61 denotes V or M.

The invention further provides a pharmaceutical composition comprising an isolated peptide of 10 to 30 amino acid residues in length which corresponds to a fragment of the ectodomain of the natural cytotoxicity receptor protein NKp44, the peptide comprising the amino acid sequence selected from the group consisting of: SEQ ID NOS: 25-44. In some embodiments, the peptide is useful in preventing or treating cancer in a subject.

In some embodiments, the pharmaceutical composition further comprises a pharmaceutically acceptable carrier.

In another aspect, the invention provides an isolated peptide of about 10 to 30 amino acid residues in length which corresponds to a fragment of the D2 domain of the extracellular domain of NKp46, the peptide comprising the amino acid sequence as set forth in SEQ ID NO: 57 (LDTATSMFLL) or SEQ ID NO: 58 (LKTATSKFFL).

In a particular embodiment, the peptide consists of about 15 to 25 amino acid residues. In another particular embodiment, the peptide consists of about 15 to 20 amino acid residues. In a particular embodiment, the peptide consists of about 20 amino acid residues. In a particular embodiment, the peptide consists of at least 14 amino acid residues. In yet another particular embodiment, the peptide consists of at least 15 amino acid residues.

In a particular embodiment, the NKp46 is human Nkp46. In a particular embodiment, the human NKp46 is an isoform selected from the group consisting of isoform a, isoform b, isoform c and isoform d.

In a particular embodiment, the D2 domain of the extracellular domain of NKp46 is selected from the group consisting of: SEQ ID NOS: 45-50. In another particular embodiment, the D2 domain of the extracellular domain of NKp46 has the amino acid sequence as set forth in SEQ ID NO: 45. In a particular embodiment, the isolated peptide corresponding to a fragment of the D2 domain of NKp46 comprises the amino acid sequence as set forth in SEQ ID NO: 57 (LDTATSMFLL). In another embodiment, said isolated peptide comprises the amino acid sequence of SEQ ID NO: 55 (TFYCRLDTATSMFLL). In another embodiment, said isolated peptide comprises the amino acid sequence of SEQ ID NO: 56 (TFFCQLKTATSKFFL).

In a particular embodiment, the isolated peptide comprises the amino acid sequence selected from the group consisting of: SEQ ID NOS: 4, 5, 6 and 55. In another particular embodiment, said isolated peptide consists of an amino acid sequence selected from the group consisting of: SEQ ID NOS: 4, 5, 6 and 55. In yet another particular embodiment, said isolated peptide consists of the amino acid sequence as set forth in SEQ ID NOS: 4.

The invention further provides a pharmaceutical composition comprising at least one isolated peptide comprising the amino acid sequence as set forth in SEQ ID NO: 57 or SEQ ID NO: 58 and a pharmaceutically acceptable carrier. According to specific embodiments, the pharmaceutical composition comprises a peptide selected from the group consisting of SEQ ID NOS: 4, 5, 6 and 55. In particular embodiments, the pharmaceutical composition is useful for treating diabetes in a subject in need thereof.

The invention further provides a method for preventing or treating diabetes, the method comprising administering to a subject in need thereof, a therapeutically effective amount of an isolated peptide of the invention; thereby preventing or treating diabetes in the subject. In some embodiments, the method comprises administering a pharmaceutical composition comprising the peptide of the invention.

The invention further provides an isolated peptide of the invention for use in preventing or treating diabetes in a subject. In a particular embodiment, the diabetes is selected from the group consisting of immune-mediated diabetes, type 1 diabetes and type 2 diabetes. In one embodiment, the diabetes is type 1 diabetes. In another embodiment, the diabetes is type 2 diabetes.

In a particular embodiment, the method for preventing or treating diabetes comprises initially administering a composition comprising a peptide of the invention at a stage of type 1 diabetes selected from the group consisting of pre-insulitis, early insulitis, pre-diabetes and overt diabetes. In a particular embodiment, the method comprises administering a composition comprising a peptide of the invention at a stage of type 1 diabetes selected from the group consisting of pre-insulitis, early insulitis, pre-diabetes, overt diabetes and a combination thereof.

In a particular embodiment, the method for preventing or treating diabetes comprises initially administering a composition comprising a peptide of the invention at a stage of type 2 diabetes selected from the group consisting of hyperinsulinemia, pre-diabetes and overt diabetes. In a particular embodiment, the method comprises administering a composition comprising a peptide of the invention at a stage of type 2 diabetes selected from the group consisting of hyperinsulinemia, pre-diabetes and overt diabetes.

In a particular embodiment, the administering is initiated following detection of impaired fasting blood glucose levels in the subject. In a particular embodiment, the administering is initiated following detection of impaired glucose tolerance levels in the subject. In a particular embodiment, the method comprises determination of fasting blood glucose levels and glucose tolerance levels in the subject prior to and subsequent to administering the composition.

In a particular embodiment, the method comprises administration of a single dose of the composition or multiple doses of the composition. In a particular embodiment, the composition is administered at weekly intervals.

In a particular embodiment, the administering is carried out by a route selected from the group consisting of parenteral, oral and transdermal.

In a particular embodiment, the method further comprises administering an immunomodulatory or immunostimulatory agent in conjunction with administering the composition of the invention. In a particular embodiment, the immunomodulatory or immunostimulatory agent is selected from the group consisting of Bacille Calmette-Guérin (BCG), heat shock protein 60 (HSP60) or a fragment thereof, roquinimex, Q fever complement-fixing antigen (QFA), anti-CD3 antibody, α-galactoslyceramide, an adjuvant and a combination thereof. In a particular embodiment, the adjuvant is selected from the group consisting of immune stimulating complexes (ISCOMS), liposomes, lipopolysaccharide, monophosphoryl lipid A, CpG DNA, muramylpeptides and a combination thereof.

In another aspect, the present invention provides a method for preventing or treating cancer, the method comprising administering to a subject in need thereof a therapeutically effective amount of an isolated peptide of 10 to 30 amino acid residues in length which corresponds to a fragment of the ectodomain of the natural killer cell receptor protein NKp44; thereby preventing or treating cancer in the subject.

The isolated peptide of NKp44 is as described hereinabove. The invention further provides an antibody, or an antigen-binding fragment thereof, specific for the isolated peptide of the invention. In a particular embodiment, the antibody is selected from the group consisting of a monoclonal antibody, a bispecific antibody, a single chain antibody and a humanized antibody. In a particular embodiment, the antibody is non-depleting for NK cells. In yet another particular embodiment, said antibody is useful for treating cancer in a subject.

In particular embodiments, said antibody is specific for an isolated peptide comprising the amino acid sequence as set forth in SEQ ID NO: 57 (LDTATSMFLL) or SEQ ID NO: 58 (LKTATSKFFL). In another particular embodiment, said antibody is specific for a peptide selected from the group consisting of SEQ ID NOS: 4, 5, 6, 55 and 56.

In another embodiment, the antibody is specific for an isolated peptide comprising the amino acid sequence selected from the group consisting of SEQ ID NOS: 31-34.

Other objects, features and advantages of the present invention will become clear from the following description and drawings.

BRIEF DESCRIPTION OF THE FIGURES

FIG. 1—Schematic representation of the D2 domain of NKp46 depicting the overlapping peptides (SEQ ID NO: 1-24). The sequence of pep4 (SEQ ID NO: 4) is shown in gray. The superscript and subscript numbers designate the peptide's N- and C-terminus, respectively.

(FIG. 9A) HeLa cells stained with NKp46D2-Ig in the presence of peptides of SEQ ID NO: 4 (denoted pep4) or SEQ ID NO: 1 (denoted mock1). Results are shown as histograms overlay. (FIG. 9B-9D) Reduced staining of NK receptor-Igs mediated by the presence of peptides is shown as % inhibition, as compared to staining without peptides. (FIG. 9B) HeLa cells stained with NKp46-Ig or NKp46D2-Ig in the presence of the indicated peptides. (FIG. 9C) CHO-K1, HeLa, HEK293T and PC3 cells stained with NKp46D2-Ig in the presence of the indicated peptides. (FIG. 9D) HeLa cells stained with NKp46D2-Ig, NKp44-Ig, NKp30-Ig, or LIR1-Ig in the presence of titrated amounts of pep4 ranging from 0.625 to 10 µg/well, or 10 µg/well of mock peptides.

(FIG. 10A) HeLa cells co-incubated with a human primary NK cell line in the presence of the peptide of SEQ ID NO: 4 (pep4) or SEQ ID NO: 1 (mock1) peptide at indicated effector:target (E:T) ratios for 4 hr. (FIG. 10B) NK cells pre-incubated with mouse polyclonal anti-NKp46 serum or with naive serum 30 min at 4° C. before being combined with target cells at 15:1 E:T cell ratio and the indicated peptides. Percentage of specific lysis was determined by flow cytometry analysis. (FIG. 10C) Comparative analysis of CD107a expression on human primary NK cells co-incubated with HeLa or 721.221 cell lines for 4 hr at the indicated E:T cell ratio, in the presence of pep4 or mock2. Cells were then washed and stained for CD107a cell surface expression.

DETAILED DESCRIPTION OF THE INVENTION

Figure 2:
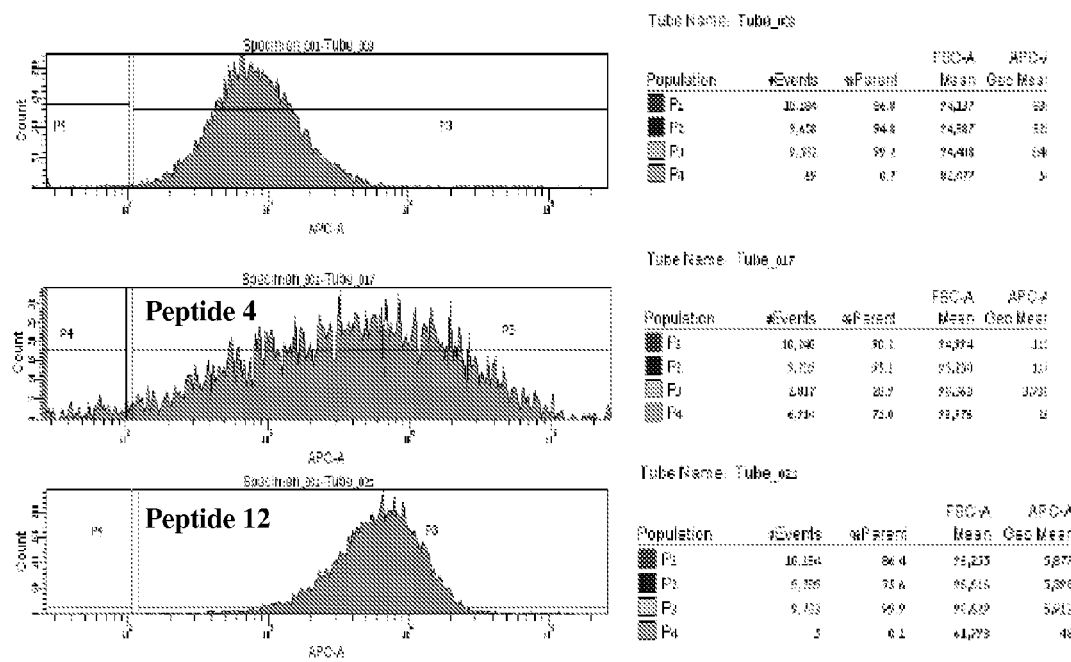
FIG. 2—Effect of peptides of SEQ ID NOS: 4 and 12 on NKp46D2-Ig staining of HeLa cells.

The present inventors disclose herein for the first time that specific peptides corresponding to portions of the D2 domain of NKp46, or to the ectodomain of NKp44 directly bind target cells or inhibit or enhance binding of the parental NK receptor domain to such target cells.

Definitions

The term "NKp46" as used herein refers to any human or non-human homolog, ortholog or isoform of the human natural cytotoxocity receptor known as NKp46, including for example those having GenBank Accession Nos. CAA04714; CAA06872; CAA06873; CAA06874; AAH42788 or NP_034876.

The term "NKp44" as used herein refers to any human or non-human homolog, ortholog or isoform of the human natural cytotoxocity receptor known as NKp44, including for example the sequences having the GenBank Accession Nos. 095944.2, NP_004819.2, NP_001186439.1, and NP_001186438.1.

The terms "subject" and "patient" as used herein refer to any single subject for whom prevention and/or treatment of diabetes is desired, including humans and non-human mammals, such as primate, bovine, ovine, canine, feline and rodent mammals. Also included are subjects involved in clinical research trials not showing any clinical sign of disease, or subjects involved in epidemiological studies, or subjects used as controls.

The term "preventing diabetes" includes but is not limited to preventing the onset of diabetes and/or preventing progression of diabetes.

The term "non-depleting antibody" refers to an antibody which does not substantially kill, destroy or eliminate a cell or organism which bears the specific antigen which is recognized by the particular antibody.

As used herein, a "peptide" is a plurality of contiguous amino acid residues comprising from at least about 3 amino acid residues to about 50 amino acid residues. A peptide may represent a fragment of a larger polypeptide product from which it is derived for example, by proteolytic cleavage or other processing mechanisms. A peptide can comprise modified amino acid residues, amino acid analogs or non-naturally occurring amino acid residues and can be interrupted by non-amino acid residues. Included within the definition are peptides that have been modified, whether naturally or by intervention, e.g., formation of a disulfide bond, glycosylation, lipidation, methylation, acetylation, phosphorylation, or by manipulation, such as conjugation with a labeling component.

As used herein the term "isolated" is meant to describe a compound of interest (e.g., a peptide) that is in an environment different from that in which the compound naturally occurs or was produced. "Isolated" is meant to include compounds that are within samples that are substantially enriched for the compound of interest and/or in which the compound of interest is partially or substantially purified.

The singular forms "a", "an", and "the" include plural referents unless the context clearly dictates otherwise. Thus, for example, reference to "an antibody" includes one or more of such antibodies and equivalents thereof known to those skilled in the art, and so forth.

Diabetes

In some embodiments, the invention provides use of a pharmaceutical composition comprising at least one isolated peptide of the invention and a pharmaceutically acceptable carrier, for treatment or prevention of diabetes.

Type 1 diabetes (also known as immune-mediated diabetes) is characterized by loss of the insulin-producing beta cells of the islets of Langerhans in the pancreas leading to insulin deficiency. Type 1 diabetes is associated a T-cell mediated autoimmune attack on beta cells, and there is no known preventive measure for the disease, which causes approximately 10% of diabetes cases in North America and Europe. Most affected people are otherwise healthy and of a healthy weight when onset occurs. Sensitivity and responsiveness to insulin are usually normal, especially in the early stages. Type 1 diabetes can affect children or adults but was traditionally termed "juvenile diabetes" because it represents a majority of the diabetes cases in children.

Type 2 diabetes (formerly called non-insulin-dependent diabetes mellitus (NIDDM), or adult-onset diabetes) is a disorder that is characterized by high blood glucose in the context of insulin resistance and relative insulin deficiency. Risk factors associated with incidence of type 2 diabetes include obesity, hypertension, elevated cholesterol (combined hyperlipidemia), metabolic syndrome and genetic background. Type 2 diabetes accounts for about 90% of diabetes cases in the U.S., and has significantly increased in incidence over the past decades, mainly due to lifestyle factors.

The classical symptoms of diabetes are polyuria (frequent urination), polydipsia (increased thirst) and polyphagia (increased hunger). Symptoms may develop quite rapidly (weeks or months) in type 1 diabetes, particularly in children. However, in type 2 diabetes symptoms usually develop much more slowly and may be subtle or completely absent. Diabetes (both types) may also cause a rapid yet significant weight loss (despite normal or even increased eating) and irreducible mental fatigue.

Patients with type 1 diabetes may also initially present with diabetic ketoacidosis, an extreme state of metabolic dysregulation characterized by the smell of acetone on the patient's breath; a rapid, deep breathing known as Kussmaul breathing; polyuria; nausea; vomiting and abdominal pain; and any of many altered states of consciousness or arousal. In severe cases, coma may follow, progressing to death.

Final diagnosis of both type 1 and type 2 diabetes is made by determination of blood glucose concentrations.

As used herein, the term "overt diabetes" refers to a diagnosis of full-blown diabetes in a subject based on plasma glucose levels, for example, in humans a fasting plasma glucose level≥7.0 mmol/l (126 mg/dl); or, in an oral glucose tolerance test, two hours after ingestion of an oral dose of 75 g, a plasma glucose level≥11.1 mmol/l (200 mg/dl); or symptoms of hyperglycemia and casual plasma glucose level≥11.1 mmol/l (200 mg/dl); or the equivalent standards determined for a non-human species. The aforementioned are widely accepted diagnostic criteria for human diabetes (World Health Organization 2006. Definition and diagnosis of diabetes mellitus and intermediate hyperglycemia. Geneva, Switzerland). Glycated hermoglobulin (hemoglobulin A1C) at or above 6.5% may also be considered diagnostic for human diabetes, although it is not uniformly accepted among health policy organizations (Mayfield Diagnosis and Classification of Diabetes Mellitus: New Criteria. Am Fam Physician. 1998 Oct. 15; 58(6):1355-62, 1369-70).

As used herein, the term "pre-diabetes" refers to the occurrence of either or both of impaired fasting glucose and impaired glucose tolerance in a subject. For example in humans, a fasting glucose level from 100 to 125 mg/dL (5.6 to 6.9 mmol/L) is indicative of impaired fasting glucose, and a plasma glucose at or above 140 mg/dL (7.8 mmol/L), but not over 200 mg/dL (11.1 mmol/L), two hours after a 75 g oral glucose load, is indicative of impaired glucose tolerance. The term also encompasses the equivalent standards determined for a non-human species.

As used herein, the term "hyperinsulinemia" refers to the occurrence of elevated levels of circulating insulin, for example a fasting serum insulin value above 19.1 μU/ml for humans, or the equivalent standard determined for a non-human species. Hyperinsulinemia is a marker of insulin resistance, a correlate of the metabolic syndrome, and an established precursor of type 2 diabetes (Carnethon et al., Risk Factors for Progression to Incident Hyperinsulinemia: The Atherosclerosis Risk in Communities Study, 1987-1998).

As used herein, the term "insulitis" refers to the occurrence of lymphocytic infiltration in the islets of Langerhans, such that affected islets have lost most of their beta cell-mass and have only residual beta cells (i.e. less than about 20% of beta cell-mass is retained). Similarly, the terms "pre-insulitis" and "early insulitis" refer to earlier stages of lymphocyte infiltration characterized by a lesser degree of beta cell loss, such that the retained beta cell-mass in pre-insulitis is from about 60 to greater than 80%, and in early insulitis it is about 20 to about 60%.

Malignant Diseases

The invention further provides a method for preventing or treating cancer, the method comprising administering to a subject in need thereof, a therapeutically effective amount of a peptide of the invention; thereby preventing or treating cancer in the subject. The invention further provides an isolated peptide of the invention for use in preventing or treating cancer in a subject.

The terms "cancer", "malignant disease", "neoplastic disease", "tumor", and the like are used interchangeably herein to refer to conditions characterized by cells which exhibit relatively autonomous growth, so that they exhibit an aberrant growth phenotype characterized by a significant loss of control of cell proliferation.

Malignant diseases include for example, hematologic cancers, bladder cancer, bone cancer, breast cancer, cervical cancer, colon cancer, endometrial cancer, gastric cancer, head and neck cancer, hepatic cancer, kidney cancer, lung cancer, melanoma, ovarian cancer, pancreatic cancer, prostate cancer, renal cancer, sarcoma, skin cancer, stomach cancer, testicular cancer and thyroid cancer. Hematologic cancers include for example, multiple myeloma (MM), acute lymphoblastic leukemia (ALL), acute myeloid leukemia (AML), chronic lymphocytic leukemia CLL), chronic myelogenous leukemia (CML), Hodgkin's disease (HD), non-Hodgkin's lymphoma and hairy cell leukemia (HCL). Additional malignant diseases include hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, lung carcinoma including small cell, non-small and large cell lung carcinoma, glioma, astrocyoma, medulloblastoma, craniopharyngioma, ependymoma, pinealoma, retinoblastoma, neuroblastoma, and rectal carcinoma.

In a particular embodiment, the cancer is selected from the group consisting of hematologic cancers, bladder cancer, bone cancer, breast cancer, cervical cancer, colon cancer, endometrial cancer, gastric cancer, head and neck cancer, hepatic cancer, kidney cancer, lung cancer, melanoma, ovarian cancer, pancreatic cancer, prostate cancer, renal cancer, sarcoma, skin cancer, stomach cancer, testicular cancer and thyroid cancer.

Peptides

Peptides for use in the methods and compositions of the invention include those having the amino acid sequences of SEQ ID NOS: 2-23, 25-44 and 55-58.

TABLE 1

NKp46- and NKp44- derived peptides

| SEQ ID NO: | Sequence |
|---|---|
| 1 | YDTPT LSVHP GPEVI SGEKV |
| 2 | LSVHP GPEVI SGEKV TFYCR |
| 3 | GPEVI SGEKV TFYCR LDTAT |
| 4 | SGEKV TFYCR LDTAT SMFLL |
| 5 | TFYCR LDTAT SMFLL LKEGR |
| 6 | LDTAT SMFLL LKEGR SSHVQ |
| 7 | SMFLL LKEGR SSHVQ RGYGK |
| 8 | LKEGR SSHVQ RGYGK VQAEF |
| 9 | SSHVQ RGYGK VQAEF PLGPV |
| 10 | RGYGK VQAEF PLGPV TTAHR |
| 11 | VQAEF PLGPV TTAHR GTYRC |
| 12 | PLGPV TTAHR GTYRC FGSYN |
| 13 | TTAHR GTYRC FGSYN NHAWS |
| 14 | GTYRC FGSYN NHAWS FPSEP |
| 15 | FGSYN NHAWS FPSEP VKLLV |
| 16 | NHAWS FPSEP VKLLV TGDIE |
| 17 | FPSEP VKLLV TGDIE NTSLA |
| 18 | VKLLV TGDIE NTSLA PEDPT |
| 19 | TGDIE NTSLA PEDPT FPADT |
| 20 | NTSLA PEDPT FPADT WGTYL |
| 21 | PEDPT FPADT WGTYL LTTET |
| 22 | FPADT WGTYL LTTET GLQKD |
| 23 | WGTYL LTTET GLQKD HALWD |
| 24 | LTTET GLQKD HALWD HTAQ |
| 25 | QSKAQ VLQSV AGQTL TVRCQ |
| 26 | VLQSV AGQTL TVRCQ YPPTG |
| 27 | AGQTL TVRCQ YPPTG SLYEK |
| 28 | TVRCQ YPPTG SLYEK KGWCK |
| 29 | YPPTG SLYEK KGWCK EASAL |
| 30 | SLYEK KGWCK EASAL VCIRL |
| 31 | KGWCK EASAL VCIRL VTSSK |
| 32 | EASAL VCIRL VTSSK PRTVA |

TABLE 1-continued

NKp46- and NKp44- derived peptides

| SEQ ID NO: | Sequence |
|---|---|
| 33 | VCIRL VTSSK PRIMA WTSRF |
| 34 | VTSSK PRTVA WTSRF TIWDD |
| 35 | PRIMA WTSRF TIWDD PDAGF |
| 36 | WTSRF TIWDD PDAGF FTVTM |
| 37 | TIWDD PDAGF FTVTM TDLRE |
| 38 | PDAGF FTVTM TDLRE EDSGH |
| 39 | FTVTM TDLRE EDSGH YWCRI |
| 40 | TDLRE EDSGH YWCRI YRPSD |
| 41 | EDSGH YWCRI YRPSD NSVSK |
| 42 | YWCRI YRPSD NSVSK SVRFY |
| 43 | YRPSD NSVSK SVRFY LVVSP |
| 44 | HYWCR IYRPS DNSVS KSVRF |
| 55 | TFYCR LDTAT SMFLL |
| 56 | TFFCQ LKTAT SKFFL |
| 57 | LDTAT SMFLL |
| 58 | LKTAT SKFFL |

In a particular embodiment, the isolated peptide corresponding to a fragment of the D2 domain of NKp46 has an amino acid sequence selected from the group consisting of: SEQ ID NOS: 2-23 and 55. In a particular embodiment, the isolated peptide corresponding to a fragment of NKp46 is selected from the group consisting of: SEQ ID NOS: 4, 5, 6 and 55. In another particular embodiment, said isolated is selected from the group consisting of: SEQ ID NOS: 4, 5 and 55. In another embodiment, said isolated peptide comprises the amino acid sequence of SEQ ID NOS: 55. In yet another particular embodiment, said isolated peptide consists of the amino acid sequence as set forth in SEQ ID NOS: 4.

In a particular embodiment, the NK receptor is selected from the group consisting of NKp46 and NKp44. In a particular embodiment, the isolated peptide corresponds to a fragment of the D2 domain of the extracellular domain of NKp46. In a particular embodiment, the isolated peptide corresponds to a fragment of the ectodomain of NKp44.

In another embodiment, the isolated peptide corresponds to a fragment of the ectodomain of NKp44. In some embodiments, the ectodomain of NKp44 comprises SEQ ID NO: 51. In another embodiment, the isolated peptide corresponding to a fragment of the ectodomain of NKp44 is selected from the group consisting of: SEQ ID NOS: 25-44. In a particular embodiment, the isolated peptide is selected from the group consisting of: SEQ ID NOS: 31-33. In yet another embodiment, the isolated peptide is SEQ ID NO: 34.

In a particular embodiment, the NK receptor is a human NK receptor. In a particular embodiment, the NK receptor is selected from the group consisting of NKp46 and NKp44. In a particular embodiment, the isolated peptide corresponds to a fragment of the D2 domain of the extracellular domain of NKp46. In a particular embodiment, the human NKp46 is an isoform selected from the group consisting of isoform a, isoform b, isoform c and isoform d. In a particular embodiment, the D2 domain of the extracellular domain of NKp46 is selected from the group consisting of: SEQ ID NOS: 45-50.

In a particular embodiment, the isolated peptide corresponds to a fragment of the ectodomain of NKp44. In a particular embodiment, the ectodomain of NKp44 comprises SEQ ID NO: 51.

TABLE 2

The extracellular region of NKp46 and NKp44 receptors

| Amino acid sequence | SEQ ID NO: |
|---|---|
| YDTPTLSVHP GPEVISGEKV TFYCRLDTAT SMFLLLKEGR SSHVQRGYGK VQAEFPLGPV TTAHRGTYRC FGSYNNHAWS FPSEPVKLLV TGDIENTSLA PEDPTFPADT WGTYLLTTET GLQKDHALWD HTAQ | 45 |
| YDTPTLSVHP GPEVISGEKV TFYCRLDTAT SMFLLLKEGR SSHVQRGYGK VQAEFPLGPV TTAHRGTYRC FGSYNNHAWS FPSEPVKLLV TGDIENTSLA PEDPTFPDHA LWDHTAQ | 46 |
| YDTPT LSVHPGPEVI SGEKVTFYCR LDTATSMFLL LKEGRSSHVQ RGYGKVQAEF PLGPVTTAHR GTYRCFGSYN NHAWSFPSEP VKLLVTGDIE NTSLAPEDPT FPADTWGTYL LTTETGLQKD HALWDHTAQ | 47 |
| YDTPT LSVHPGPEVI SGEKVTFYCR LDTATSMFLL LKEGRSSHVQ RGYGKVQAEF PLGPVTTAHR GTYRCFGSYN NHAWSFPSEP VKLLVTGDIE NTSLAPEDPT FPDHALWDHT AQ | 48 |
| LKLVVTGLYD TPNLWVYPRP EVTLGENVTF FCQLKTATSK FFLLKERGSN HIQNKYGNIQ AEFPMGPVTR AHRGTYRCFG SYNDYAWSFP SEPVTLLITG GVENSSLAPT DPTSSLDYWE FDLSTNESGL QKDSAFWDHT TQ | 49 |
| YDTPNLWVYP QPEVTLGENV TFFCQLKTAT SKFFLLKERG SNHIQNKYGN IQAEFPMGPV TRAHRGTYRC FGSYNDYAWS FPSEPVTLLI TGGVENSSLA PTDPTSSLDY WEFDLSTNES GLQKDSAFWD HTTQ | 50 |

TABLE 2-continued

The extracellular region of NKp46 and NKp44 receptors

| Amino acid sequence | SEQ ID NO: |
|---|---|
| QSKAQVLQSV AGQTLTVRCQ YPPTGSLYEK KGWCKEASAL<br>VCIRLVTSSK PRTVAWTSRF TIWDDPDAGF FTVTMTDLRE<br>EDSGHYWCRI YRPSDNSVSK SVRFYLVVSP | 51 |
| MSSTLPALLC VGLCLSQRIS AQQQTLPKPF IWAEPHFMVP<br>KEKQVTICCQ GNYGAVEYQL HFEGSLFAVD RPKPPERINK<br>VKFYIPDMNS RMAGQYSCIY RVGELWSEPS NLLDLVVTEM<br>YDTPTLSVHP GPEVISGEKV TFYCRLDTAT SMFLLLKEGR<br>SSHVQRGYGK VQAEFPLGPV TTAHRGTYRC GSYNNHAWSF<br>PSEPVKLLVT GDIENTSLAP EDPTFPADTW GTYLLTTETG<br>LQKDHALWDH TAQNLLRMGL AFLVLVALVW FLVEDWLSRK<br>RTRERASRAT WEGRRRLNTQ TL | 52 |
| MGMPMGSLQP LATLYLLGML VASCLGRLRV PYDTPTLSVH<br>PGPEVISGEK VTFYCRLDTA TSMFLLLKEG RSSHVQRGYG<br>KVQAEFPLGP VTTAHRGTYR CFGSYNNHAW SFPSEPVKLL<br>VTGDIENTSL APEDPTFPDT WGTYLLTTET GLQKDHALWD<br>PEPKSSDKTH TCPPCPAPEF EGAPSVFLFP PKPKDTLMIS<br>RTPEVTCVVV DVSHEDPEVK FNWYVDGVEV HNAKTKPREE<br>QYNSTYRVVS VLTVLHQDWL NGKEYKCKVS NKALPAPIEK<br>TISKAKGQPR EPQVYTLPPS RDELTKNQVS LTCLVKGFYP<br>SDIAVEWESN GQPENNYKTT PPVLDSDGSF FLYSKLTVDK<br>SRWQQGNVFS CSVMHEALHN HYTQKSLSLS PGK | 53 |
| MGMPMGSLQP LATLYLLGML VASCLGRLRV PYDTPTLSVH<br>PGPEVISGEK VTFYCRLDTA TSMFLLLQEG QSSQVQQGYG<br>KVQAEFPLGP VTTAHRGTYR CFGSYNNHAW SFPSEPVKLL<br>VTGDIENTSL APEDPTFPDT WGTYLLTTET GLQKDHALWD<br>PEPKSSDKTH TCPPCPAPEF EGAPSVFLFP PKPKDTLMIS<br>RTPEVTCVVV DVSHEDPEVK FNWYVDGVEV HNAKTKPREE<br>QYNSTYRVVS VLTVLHQDWL NGKEYKCKVS NKALPAPIEK<br>TISKAKGQPR EPQVYTLPPS RDELTKNQVS LTCLVKGFYP<br>SDIAVEWESN GQPENNYKTT PPVLDSDGSF FLYSKLTVDK<br>SRWQQGNVFS CSVMHEALHN HYTQKSLSLS PGK | 54 |

Peptides for use in the compositions of the invention may further comprise a modification, on the condition that such modified peptide(s) retain biological activity of the original peptides disclosed herein.

The terms "derivative" and "functional variant" are used interchangeably herein to refer to a peptide which contains one or more modifications to the primary amino acid sequence of NKp46 or NKp44 peptide and retains its binding properties. Modifications are desired, for example, to 1) enhance a property of the peptide, such as increased stability within a multimeric complex and/or more efficient presentation to T cells; 2) provide a novel activity or property to the peptide, such as addition of an antigenic epitope or addition of a detectable moiety; 3) provide a different amino acid sequence that produces the same or similar immunostimulatory properties, or 4) improve the pharmacological characteristics of the pharmaceutical composition.

Modifications to peptides can be made to nucleic acids which encode the peptides, and can include deletions, point mutations, truncations, amino acid substitutions and additions of amino acids. Alternatively, modifications can be made directly to the peptide, such as by glycosylation, side chain oxidation, phosphorylation, cleavage, addition of a linker molecule, addition of a detectable moiety, such as biotin, addition of a fatty acid, amino acid substitution and the like.

Amino acid substitution to produce peptide functional variants preferably involves conservative amino acid substitution i.e., replacing one amino acid residue with another that is biologically and/or chemically similar, e.g., a hydrophobic residue for another, or a polar residue for another. Examples of conservative substitutions of amino acids include substitutions made amongst amino acids within the following groups: (a) Met, Ile, Leu, Val; (b) Phe, Tyr, Trp; (c) Lys, Arg, His; (d) Ala, Gly; (e) Ser, Thr; (f) Gln, Asn; and (g) Glu, Asp. The peptides of the present invention can be prepared by any suitable means, such as synthetically using standard peptide synthesis chemistry or by using recombinant DNA technology.

The peptides may be modified so as to enhance their immunostimulatory activity, such that the modified peptides have immunostimulatory activity greater than a peptide of the wild-type sequence. Alternately, peptide modifications may serve to increase their binding affinity to target cell, and thus increase the clinical efficacy of a pharmaceutical composition as described herein. Generally, any substitutions, additions or deletions between epitopic and/or conformationally important residues will employ amino acids or moieties chosen to avoid stearic and charge interference that might disrupt binding.

Modifications also encompass fusion proteins comprising all or part of a peptide amino acid sequence with a related or unrelated protein or polypeptide.

Additional amino acids can be added to the termini of a peptide to provide for ease of linking peptides one to another, or for coupling a peptide to a multimeric complex. Addition of amino acids may also be used for modifying the physical or chemical properties of the peptide and/or multimeric complex. Suitable amino acids, such as tyrosine, cysteine, lysine, glutamic or aspartic acid, can be introduced at the C- or N-terminus of the peptide. In addition, the peptide can differ from the natural sequence by being modified for example, by N-terminal acylation, N-terminal amidation, or C-terminal amidation. In some instances these modifications may provide sites for linking to a support or other molecule, thereby providing a linker function.

Modifications also encompass introduction of one or more non-natural amino acids, introduced so as to render a peptide non-hydrolyzable or less susceptible to hydrolysis, as compared to the original peptide. To provide such peptides, one may select one or more modified NKp46 or NKp44 peptides from a library of non-hydrolyzable peptides, such as peptides containing one or more D-amino acids or peptides containing one or more non-hydrolyzable peptide bonds linking amino acids. Alternatively, one can select peptides which have optimal biological, and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis. Alternatively, potentially susceptible peptide bonds can be identified by comparing the amino acid sequence of a peptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Non-hydrolyzable peptide bonds are known in the art, along with procedures for synthesis of peptides containing such bonds. Non-hydrolyzable bonds include, but are not limited to, -psi[$CH_2NH$]— reduced amide peptide bonds, -psi[$COCH_2$]— ketomethylene peptide bonds, -psi[CH(CN)NH]— (cyanomethylene)amino peptide bonds, -psi[$CH_2CH(OH)$] hydroxyethylene peptide bonds, -psi[$CH_2O$]— peptide bonds, and -psi[$CH_2S$]— thiomethylene peptide bonds.

Modifications also encompass peptides that have conjugated thereto a substance, such as a radioactive moiety, an enzyme, a fluorescent moiety, a solid matrix, a carrier, and a cell epitope. The substance can be conjugated to the peptide at any suitable position, including the N and C termini and points in between, depending on the availability of appropriate reactive groups in the side chains of the constituent amino acids of the peptide of interest. Additionally, the substance can be conjugated directly to the peptide or indirectly by way of a linker. Radiolabels include $^3H$, $^{14}C$, $^{32}P$, $^{35}S$, $^{125}I$, and other suitable radioactive moieties for use in various radioimmunoassays and the like. Fluorescent moieties include fluorescein, rhodamine, and other suitable fluorescent labels for use in fluorescent assays and the like. Enzymes include alkaline phosphatase, BirA and other suitable enzymes useful for any suitable purpose, including as a marker in an assay procedure. Carriers include immunogenic lipids, proteins, and other suitable compounds, such as a liposome or bovine serum albumin Peptides for use in the compositions of the invention can be prepared using any suitable means. Because of their relatively short size (generally less than about 30 amino acids), the peptides can be synthesized in solution or on a solid support in accordance with conventional peptide synthesis techniques. Various automatic synthesizers are commercially available (for example, from Applied Biosystems) and can be used in accordance with known protocols (see, for example, Stewart and Young (1984) *Solid Phase Peptide Synthesis*, 2nd ed., Pierce Chemical Co.; Tam et al. (1983) J. Am. Chem. Soc. 105:6442; Merrifield (1986) Science 232:341-347).

Alternatively, recombinant DNA technology may be employed, wherein a nucleotide sequence that encodes a peptide of interest is inserted into an expression vector, transformed or transfected into a suitable host cell and cultivated under conditions suitable for expression. These procedures are generally known in the art, as described generally in Sambrook et al. (2001) *Molecular Cloning, A Laboratory Manual* 3rd ed. Cold Spring Harbor Press, Cold Spring Harbor, N.Y., and Ausubel et al., eds. (1987) *Current Protocols in Molecular Biology* John Wiley and Sons, Inc., N.Y., and U.S. Pat. Nos. 4,237,224, 4,273,875, 4,431,739, 4,363,877 and 4,428,941.

As the coding sequence for peptides of the length contemplated herein can be synthesized by chemical techniques, for example, the phosphotriester method of Matteucci et al., J. Am. Chem. Soc., 103, 3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. For expression of the fusion proteins, the coding sequence will be provided with operably linked start and stop codons, promoter and terminator regions and usually a replication system to provide an expression vector for expression in a suitable cellular host. For example, promoter sequences compatible with bacterial hosts are provided in plasmids containing convenient restriction sites for insertion of the desired coding sequence. The resulting expression vectors are transformed into suitable bacterial hosts. Yeast or mammalian cell hosts may also be used, employing suitable vectors and control sequences.

In addition, peptides produced by recombinant methods as a fusion to proteins that are one of a specific binding pair, enable purification of the fusion protein by means of affinity reagents, followed by proteolytic cleavage, usually at an engineered site to yield the desired peptide (see for example Driscoll et al. (1993) J. Mol. Bio. 232:342-350).

NKp46 Proteins and Production Thereof

The terms "protein" and "polypeptide" are used interchangeably herein to refer to polymeric forms of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

In another embodiment, the peptide consists of at least 13, at least 14, at least 15 amino acid residues. In another embodiment, the peptide consists of at most 20, at most 21, at most 22, at most 22, at most 23, at most 24, at most 25, at most 25, at most 26, at most 27, at most 28, at most 29 or at most 30 amino acid residues. Each possibility represents a separate embodiment of the present invention.

A protein of interest or fragment thereof for use in the present invention can be obtained in isolated form by expression of a recombinant nucleic acid encoding the polypeptide or by chemical synthesis.

As used herein, a "fusion protein" or "chimeric peptide" refers to a protein or polypeptide which comprises a first segment which is a first naturally occurring protein or polypeptide or a fragment thereof, fused to a second segment which is a different protein or polypeptide or a fragment thereof.

As used herein, a "protein conjugate" or "protein multimer" interchangeably refer to a complex structure of two or more associated polypeptide chains i.e. protein subunits, optionally comprising one or more linkers or spacers. The subunits may be distinct one from the other but also at least some of the subunits may be identical, and the associations between and among the various subunits and linkers may be by covalent, non-covalent, ionic or other types of interactions.

The term "recombinant nucleic acid molecule" as used herein refers to a nucleic acid molecule that is comprised of segments of nucleic acid joined together by means of molecular biological techniques.

The term "recombinant protein" or "recombinant polypeptide" as used herein refers to a protein molecule that is expressed from a recombinant nucleic acid molecule.

The polypeptides embraced by the invention also include fusion proteins that contain either the extracellular region or a fragment of it fused to an unrelated amino acid sequence.

The unrelated sequences can be additional functional domains or signal peptides. For example, a fusion protein may include a fragment of the NKp46 D2 domain (e.g., a peptide of SEQ ID NO: 4) as a first segment, and at least one heterologous protein as a second segment. Examples of suitable heterologous proteins include immunoglobulins, cytokines, immunomodulatory proteins or peptides, an NK receptor other than NKp46, hormones, growth factors and fragments thereof. In one particular embodiment, the heterologous protein is the Fc region of IgG1.

The polypeptides can also be those with conservative amino acid substitutions, for example one, two, three, four, five, six, seven, eight, nine, 10 or more such substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The polypeptides can also be those with amino acid deletions or additions, as long as any such mutations do not substantially detract from the ability of the protein to exert its desired biological activity.

Amino acid substitutions may be carried out to eliminate glycosylation sites in the D2 domain peptide. Such substitutions are disclosed for example in US Patent Application Publication No. 2007/0203054 Amino acid substitutions may be carried out to eliminate certain ligand binding sites in the D2 domain, such as heparin binding sites. Such substitutions are disclosed for example in WO 2005/051973. The amino acid substitution may be at a residue selected from threonine 125, threonine 225, lysine 157, lysine 170, arginine 160, arginine 166, histidine 163, asparagine 216, or a combination thereof, wherein the numbers correspond to the residue positions of NKp46 of SEQ ID NO: 52. Exemplary amino acid substitution include T125A; T225A; T225S; T225N; K157Q; R160Q; H163Q; R166Q; K170T; N216A and any combination thereof; wherein the numbers correspond to the residue positions of NKp46 of SEQ ID NO: 52.

The terms "polynucleotide" and "nucleic acid" are used interchangeably herein to refer to polymeric forms of nucleotides of any length, either ribonucleotides or deoxynucleotides, including but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. Further included are mRNA or cDNA that comprise intronic sequences (see, e.g., Niwa et al. (1999) Cell 99(7):691-702). The backbone of the polynucleotide can comprise sugars and phosphate groups (as typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) Nucl. Acids Res. 24:1841-1848; Chaturvedi et al (1996) Nucl. Acids Res. 24:2318-2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component, capping, substitution of one or more of naturally occurring nucleotides with an analog, and introduction of means for attaching the polynucleotide to proteins, metal ions, labeling components, other polynucleotides, or a solid support.

A NKp46 or NKp44 gene or protein can be identified based on its similarity to the relevant NKp46 gene or protein, respectively. For example, the identification can be based on sequence identity. Polypeptides may be produced by recombinant methods using nucleic acids encoding the corresponding polypeptide, or alternately may be extracted from tissues, or chemically produced. The determination of percent identity between two sequences is accomplished using the mathematical algorithm of Karlin and Altschul (1993) Proc. Natl. Acad. Sci. USA 90:5873-5877. Such an algorithm is incorporated into the BLASTN and BLASTP programs of Altschul et al. (1990) J. Mol. Biol. 215, 403-410. BLAST nucleotide searches are performed with the BLASTN program to obtain nucleotide sequences homologous to NKp46 encoding nucleic acids. BLAST protein searches are performed with the BLASTP program to obtain amino acid sequences homologous to the NKp46 polypeptide. To obtain gapped alignments for comparative purposes, Gapped BLAST is utilized as described in Altschul et al (1997) Nucleic Acids Res. 25:3389-3402. When utilizing BLAST and Gapped BLAST programs, the default parameters of the respective programs (e.g., XBLAST and NBLAST) are used.

Hybridization can also be used as a measure of homology between two nucleic acid sequences. An NKp46-encoding nucleic acid sequence, or a portion thereof, can be used as a hybridization probe according to standard hybridization techniques. The hybridization of an NKp46probe to DNA or RNA from a test source (e.g., a mammalian cell) is an indication of the presence of NKp46 DNA or RNA in the test source. Hybridization conditions are known to those skilled in the art (See, e.g. Current Protocols in Molecular Biology, John Wiley & Sons, N.Y., 6.3.1-6.3.6, (1991)).

Recombinant NKp46 expression vectors that contain a NKp46 D2 domain coding sequence operably linked to transcriptional/translational regulatory elements may be produced. Methods well-known to those skilled in the art can be used to construct such expression vectors (See, for example, Sambrook et al, Molecular Cloning: A Laboratory Manual (2nd Ed.) Cold Spring Harbor Laboratory, N.Y., (1989); and Ausubel et al., Current Protocols in Molecular Biology Green Publishing Associates and Wiley Interscience, N.Y., (1989)).

Nucleic acids encoding NKp46 may be obtained from cells of a human or non-human subject, in particular NK cells, using appropriate oligonucleotide primers and amplification techniques, and the amplified DNA is thereafter ligated into an appropriate expression vector.

The expression vectors may encode, in addition to an NKp46 polypeptide, a second sequence unrelated to NKp46, such as a reporter, a marker, a signal peptide, or a heterologous protein sequence useful for prevention or treatment of diabete or cancer. Recombinant nucleic acid molecules can contain a signal sequence that is the native signal sequence of NKp46 or an heterologous signal sequence. The full length NKp46 polypeptide, or a fragment thereof, may be fused to such signal sequences and/or additional polypeptides. Similarly, the nucleic acid molecules of the invention can encode the mature form of NKp46 or a form that includes an exogenous polypeptide that facilitates secretion.

Accordingly, the nucleic acid encoding NKp46 can form part of a hybrid gene encoding additional polypeptide sequences. Generally, the hybrid gene will encode a polypeptide with a first segment and a second segment; the first segment being a NKp46 fragment and the second portion being for example, an immunoglobulin, a cytokine, an immunomodulatory protein or peptide, an NK receptor other than NKp46, a hormone, a growth factor or a fragment thereof. One example of a suitable the heterologous protein fragment is an immunoglobulin fragment, in particular the Fc region of IgG1. In a particular embodiment, the hybrid gene encodes a fusion protein comprising the D2 domain or a fragment thereof as the first segment, and the Fc region of IgG1 as the second segment.

Expression systems that may be used for production of NKp46 and other recombinant proteins include but are not limited to microorganisms such as bacteria, yeast, plant cell systems, insect cell systems or mammalian cell systems, which may be transformed, infected or transfected, as the case may be, with appropriate recombinant expression vectors or constructs containing the relevant nucleic acid molecule. Also useful as host cells are primary or secondary cells obtained directly from a mammal and transfected with a plasmid vector or infected with a viral vector.

Cells transfected or transduced with such expression vectors can then be used, for example, for large or small scale in vitro production of a NKp46 polypeptide or fragment thereof by methods known in the art. Such methods involve culturing the cells under conditions which maximize production of the polypeptide or antigenic fragment and isolating it from the cells or from the culture medium.

Antibodies

The term "antibody" is used herein in the broadest sense and specifically encompasses monoclonal antibodies, humanized antibodies, polyclonal antibodies, multispecific antibodies (e.g., bispecific antibodies), single chain antibodies and antibody fragments (e.g., F(ab')$_2$, Fab', Fab, Fv) so long as they bind specifically to a target antigen or epitope of interest.

The term "epitope" as used herein refers to that portion of an antigen that is specifically recognized by a particular antibody and makes contact with the antigen binding region of that antibody. When a protein or fragment of a protein is immunogenic in a host animal, numerous regions of the protein may induce the production of antibodies which bind specifically to a given region or three-dimensional structure on the protein; these regions or structures are referred to as "epitopes" or "antigenic determinants". An antigenic determinant may compete with the intact antigen which elicited the immune response, for binding to an antibody. An epitope may itself be a region of an antibody, for example the antigen binding region, or a species-specific Fc region.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries, as is known in the art, for example using techniques such as those described in Clackson et al. (1991) Nature 352:624-628 and Marks et al. (1991) J. Mol. Biol. 222:581-597.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

Chimeric antibodies are typically prepared by splicing the genes (of one species) for an antibody molecule specific for a particular antigen together with genes from another species of antibody molecule of appropriate biological activity. It can be desirable to transfer the antigen binding regions (e.g., Fab', F(ab')$_2$, Fab, Fv, or hypervariable regions) of antibodies from one species into the framework of an antibody from another species by recombinant DNA techniques to produce a chimeric molecule. Methods for producing such molecules are described in, for example, U.S. Pat. Nos. 4,816,567; 4,816, 397; 5,693,762, and 5,712,120. A human monoclonal antibody or portion(s) thereof can be identified by screening a human B-cell cDNA library for nucleic acid molecules that encode antibodies that specifically bind to a tumor associated antigen according to the method generally set forth by Huse et al. (Science 246:1275 81 (1989)). The nucleic acid molecule can then be cloned and amplified to obtain sequences that encode the antibody (or antigen-binding domain) of the desired specificity. Phage display technology offers another technique for selecting antibodies that bind to tumor associated antigens, fragments, derivatives or analogs thereof (see, e.g., International Patent Publications WO 91/17271 and WO 92/01047; Huse et al., supra.)

Techniques for the production of single chain antibodies are described for example in U.S. Pat. Nos. 4,946,778 and 5,969,108.

Bi-specific antibodies can be monoclonal antibodies that have binding specificities for at least two different antigens.

For example, one of the binding specificities can be for NKp46D2 and the other one is for any other antigen, for example a different NK receptor e.g. NKG2D. Methods of generating bi-specific antibodies are disclosed for example, in Suresh et al (Methods in Enzymology 121:210 (1986)).

Antibodies produced by any method may be purified by known methods, as described for example, in Harlow and Lane, Using Antibodies, A Laboratory Manual, Cold Spring Harbor Laboratory, New York (1999).

The terms "specifically interacts" and "specifically binds" and related grammatical terms are used herein interchangeably to refer to high avidity and/or high affinity binding between an antibody and its epitope. Antibody binding to its epitope is stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g., by use of appropriate controls.

Immunoassays for detecting specific antibodies to peptide fragments of NKp46 or NKp44 (also respectively referred to herein as "anti-NKp46 peptide antibody" and "anti-NKp44 peptide antibody") samples are known in the art and may be readily used for detecting antibodies according to the present invention. Suitable immunoassays include for example, radioimmunoassay, (RIA), fluorescent immunoassays, (FIA), enzyme-linked immunosorbant assays (ELISA), "sandwich" immunoassays, gel diffusion precipitation reactions, immunodiffusion assays, precipitation reactions, agglutination assays and immunoelectrophoresis assays (see for example, Harlow and Lane, Using Antibodies, A Laboratory Manual, Cold Spring Harbor Laboratory, New York (1999)).

Detection of antibody can be carried out using surface plasmon resonance, in which NKp46 peptide is bound to an appropriate solid substrate is exposed to the sample. Binding of specific antibody to an NKp46 peptide on the solid substrate results in a change in the intensity of surface plasmon resonance that can be detected qualitatively or quantitatively by an appropriate instrument, e.g., a Biacore™ apparatus.

Pharmaceutical Compositions and Methods of Administration

For use in the methods of the invention, an isolated peptide corresponding to the extracellular portion of NKp46 or NKp44, or an antibody specific for such a peptide fragment may be formulated in a conventional manner using one or more pharmaceutically acceptable carriers, stabilizers or excipients (vehicles) to form a pharmaceutical composition as is known in the art, in particular with respect to protein active agents. Carrier(s) are "pharmaceutically acceptable" in the sense of being compatible with the other ingredients of the composition and not deleterious to the recipient thereof.

Suitable carriers typically include physiological saline, ethanol polyols such as glycerol or propylene glycol Ringer's solutions, dextrose solution, and Hank's solution. In addition, the pharmaceutical composition or formulation may also include other carriers, adjuvants, or nontoxic, nontherapeutic, nonimmunogenic stabilizers and the like. A therapeutically effective dose refers to that amount of protein or its antibodies, which prevent or ameliorate the symptoms signs of a particular disease e.g. type 1 diabetes. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Further examples of suitable pharmaceutical carriers are well known in the art and include phosphate buffered saline solutions, water, emulsions, such as oil in water emulsions, various types of wetting agents, sterile solutions etc. Compositions comprising such carriers can be formulated by well known conventional methods.

The protein or peptide may be formulated as neutral or salt forms. Pharmaceutically acceptable salts include the acid addition salts (formed with free amino groups) and which are formed with inorganic acids such as hydrochloric or phosphoric acids, or such organic acids such as acetic, oxalic, tartaric and maleic. Salts formed with the free carboxyl groups may also be derived from inorganic bases such as sodium, potassium, ammonium, calcium, or ferric hydroxides, and organic bases as isopropylamine, trimethylamine, 2-ethylamino ethanol, histidine and procaine.

The compositions may be suitably formulated for intravenous, intramuscular, subcutaneous, or intraperitoneal administration and conveniently comprise sterile aqueous solutions, which are preferably isotonic with the blood of the recipient. Such formulations are typically prepared by dissolving solid active ingredient in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

The compositions may incorporate a stabilizer, such as for example polyethylene glycol, proteins, saccharides (for example trehalose), amino acids, inorganic acids and admixtures thereof. Stabilizers are used in aqueous solutions at the appropriate concentration and pH. The pH of the aqueous solution is adjusted to be within the range of 5.0-9.0, preferably within the range of 6-8. In formulating the protein, anti-adsorption agent may be used. Other suitable excipients may typically include an antioxidant such as ascorbic acid.

The compositions may be formulated as controlled release preparations which may be achieved through the use of polymer to complex or absorb the proteins. Appropriate polymers for controlled release formulations include for example polyester, polyamino acids, polyvinyl, pyrrolidone, ethylenevinylacetate, and methylcellulose. Another possible method for controlled release is to incorporate the antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

The composition of the invention may preferably be administered parenterally, such as by injection, intravenous infusion, subcutaneously, intramuscularly or intraperitoneally.

Antibodies are generally administered in the range of about 0.1 to about 20 mg/kg of patient weight, commonly about 0.5 to about 10 mg/kg, and often about 1 to about 5 mg/kg. In this regard, it is preferred to use proteins having a circulating half-life of at least 12 hours, preferably at least 4 days, more preferably up to 21 days. In some cases it may be advantageous to administer a large loading dose followed by periodic (e.g., weekly) maintenance doses over the treatment period. Proteins, including antibodies can be delivered by slow-release delivery systems, pumps, and other known delivery systems for continuous infusion. Dosing regimens may be varied to provide the desired circulating levels of a particular protein based on its pharmacokinetics. Thus, doses will be calculated so that the desired circulating level of therapeutic agent is maintained.

The pharmaceutical compositions for use in the methods of the invention may be alternatively be prepared and administered in formulations suitable for oral, topical or transdermal administration.

When oral preparations are desired, the compositions may be combined with excipients, such as lactose, sucrose, starch, talc magnesium stearate, crystalline cellulose, methyl cellulose, carboxymethyl cellulose, glycerin, sodium alginate or gum arabic.

The pharmaceutical compositions of the invention may be manufactured in a manner which is itself known to one skilled in the art, for example, by means of conventional mixing, granulating, dragee-making, softgel encapsulation, dissolving, extracting, or lyophilizing processes.

Suitable excipients are, in particular, fillers such as saccharides, e.g., lactose or sucrose, mannitol or sorbitol; cellulose preparations and/or calcium phosphates, e.g., tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Materials and Methods
Cells

Cell lines used were as follows: HeLa—human cervical adenocarcinoma (ATCC no. CCL-2), HEK293T-SV40 large T antigen-transfected HEK293 cells (ATCC no. CRL-11268), PC-3—human prostate adenocarcinoma (ATCC no. CRL-1435), 721.221—Epstein-Barr virus-transformed human B cells and MIN-6—secreting pancreatic beta cell line (Miyazaki J. 1990). Wild type CHO K1 cells and the mutant derivatives CHO pgsA-745 and CHO pgsD-677 were kindly supplied by Dr. Jeff Esko and have been characterized in detail elsewhere (Lanier, L. L. Annu Rev Immunol 23, 225-274 (2005); Mandelboim, 2001, ibid.).

Antibodies and Recombinant NK (rNK) Receptors

The following antibodies were used: anti-NKp46 mAb (R&D Systems, MAB 1850), and biotin-conjugated mouse anti-human CD107a/LAMP-1 mAb (SouthernBiotech, 9835-08). APC-conjugated F(ab')2 goat anti-human IgG, APC-conjugated F(ab')2 goat anti-mouse IgG, and APC-conjugated Streptavidin (Jackson ImmunoResearch, 109-136-098/115-136-068/016-130-084 respectively). Generation of mouse polyclonal anti-NKp46 or naive serum was previously described (Aktas et al. Cell Immunol 254, 149-154 (2009)). The production of NKp46-Ig, NKp30-Ig, NKp46D2-Ig and LIR1-Ig was described elsewhere (Alter et al. J Immunol Methods 294, 15-22 (2004); Arnon, T. I. et al. *Eur J Immunol* 31, 2680-2689 (2001)). To generate the recombinant NKp46-R145Q mutation (Accession no. NP_004820.1), a construct coding for NKp46-T225N-Ig that binds cellular ligands similar to NKp46-Ig (Arnon, T. I. et al. *Blood* 103, 664-672 (2004)) and mutated arginine to glutamine (R145Q) were employed. In all experiments involving NKp46-R145Q-Ig, control rNKp46 was parental NKp46-T225N-Ig.

NKp46-derived Peptides

Peptides were synthesized with/without biotin using PEPscreen® technology which is a peptide synthesis platform that utilizes Fmoc chemistry (Sigma-Aldrich). Peptides covered the NKp46D2 and the hinge region (AA 121 to 254, Acc. no. NP_004820.1). Selected peptides were also ordered from BioSight (BioSight Ltd. Israel). Stock solutions of peptides (2 mg/ml) were solubilized in DDW-10% DMSO and stored in frozen aliquots.

Constructs and Transfections cDNA for full length NKp46 (NM_001145457.1) was cloned into the HindIII and BamHI sites of the pECFPn1 and pEYFPn1 vectors (Clontech Laboratories, Inc), to generate pNKp46-ECFP or pNKp46-EYFP fusion constructs, respectively. The NKp46 insert included an upstream Kozak consensus sequence (GCCACC), as well as an additional two bases (GC) following the NKp46 cDNA to keep it in frame with the ECFP/EYFP sequences located at the C-terminus of the resulting fusion protein. $3 \times 10^5$ HEK 293T cells were plated in 3 ml complete DMEM in a 6-well plate. After 15 hrs, the media was replaced, and the cells were transfected with 3.5 µg pNKp46-ECFP and/or pNKp46-EYFP. The transfections were performed using Turbofect transfection reagent (Fermentas International Inc., R0531) following package instructions, using 1.5 µl reagent per 1 µg transfected DNA. Transfection efficiency was tested using a FACSCantoII (BD Bioscience).

Flow Cytometry

Binding of rNK receptors and binding inhibition assays were performed as follows: $1 \times 10^5$ target cells were incubated with 2 µg of the NK receptor-Ig and 5 or 10 µg of the peptides in staining solution consisting of 0.5% (w/v) BSA and 0.05% sodium azide in PBS at 4° C. for 1.5 hrs. Then, cells were washed and stained with APC-conjugated anti-human IgG. Dead cells were detected with propidium iodide (PI). Percentage of inhibition was calculated as the percent of the cell population showing a reduced staining by the NK receptor-Ig in the presence of peptides as compared to reference positive staining by the NK receptor-Ig without peptides. To assess the direct binding of peptides to target cells, 1×10^5 tumor cells were incubated with 10 µg biotin conjugated peptides for 1 hr at 4° C., washed, stained with APC-conjugated Streptavidin and analyzed by FACS. Flow cytometry was performed using a FACSCanto II or FACScalibur (BD Bioscience) and results were analyzed using Diva 6.1.2 or CellQuest 3.3, respectively.

Isolation and Culture of Primary NK Cells

NK cells were isolated from the peripheral blood of healthy donors using a human NK cell isolation kit (Miltenyi Biotec). NK purity was greater than 90% (CD3⁻CD56⁺). Purified NK cells were cultured in CellGro SCGM serum-free medium (CellGenix, 2001) supplemented with 10% heat inactivated human plasma from healthy donors, 1 mM sodium pyruvate, 2 mM L-glutamine, MEM non-essential amino acids, 1% penicillin/streptomycin, 10 mM HEPES (Gibco™) and 300 IU/ml of human IL-2 (Biological Industries Israel Ltd).

Cytotoxicity and CD107a Degranulation Assays for NK Cell Activity

The flow cytometry cytotoxicity assay was previously described (Flodstrom et al. *Diabetes* 48, 706-713 (1999)). Effector human primary NK cells were labeled with CellTrace CFSE (Invitrogen, C3554). Analysis of 7-AAD for negative-CFSE target tumor cells was performed using a FACSCantoII and data were analyzed by Diva 6.1.2. For blocking experiments, NK cells were pre-incubated with mouse polyclonal anti-NKp46 serum or with naive serum 30 min at 4° C. before being combined with target cells. The NK degranulation assay was performed as previously described (Raulet, D. H. *Nat Rev Immunol* 3, 781-790 (2003); Biassoni, R. et al. *Eur J Immunol* 29, 1014-1020 (1999)).

Kinetic Analysis by Surface Plasmon Resonance

The ProteOn™ XPR36 protein interaction array system, NLC chip and ProteOn Manager 2.1 version 2.1.0.38 (Bio-Rad Laboratories) were employed to measure the affinity of rNK receptors to NKp46-derived peptides. The ligand immobilization process was performed with PBS-0.005% Tween 20 (Sigma-Aldrich, P7949) at a flow rate of 30 µl/min Ligand binding (NKp46-derived peptides) ranged between 200 to 500 RU. Different analyte concentrations (5000 to 312.5 nM or 2000 to 125 nM, and 0 nM) of rNK were injected, each followed by regeneration of the surface using 50 mM NaOH. Kinetic measurements: Data processing was done using the 1:1 Langmuir binding model.

Example 1

Isolated Peptides Derived from the Sequence of NKp46 and Activity Thereof

The D2 domain (membrane proximal) of NKp46 was devised into a series of 24 overlapping peptides, each 20 amino acids in length with an overlap region of 15 amino acids (FIG. 1). The constructed peptides correspond to SEQ ID NOS: 1-24.

The peptides were tested for: (i) direct binding to human cancer cells, MIN6 murine beta cell line and primary mouse beta cells; (ii) effect on binding of the fusion protein NKp46D2-Ig (SEQ ID NO: 53) to human cancer cells, MIN6 murine beta cell line and primary mouse beta cells.

Protocol

Target cells were incubated for 1.5 hr with 2 µg/well NKp46D2-Ig and 10 µg/well of each peptide. NKp46D2-Ig binding intensity was determined by flow cytometry, using fluorescent 2Ab (goat anti-mouse monoclonal antibody). Biotin-conjugated peptides were employed separately (10 µg/well at 100 µl) to assess direct binding of the peptides to target cells using fluorescent Streptavidin as the second step.

Results

Figure 4:
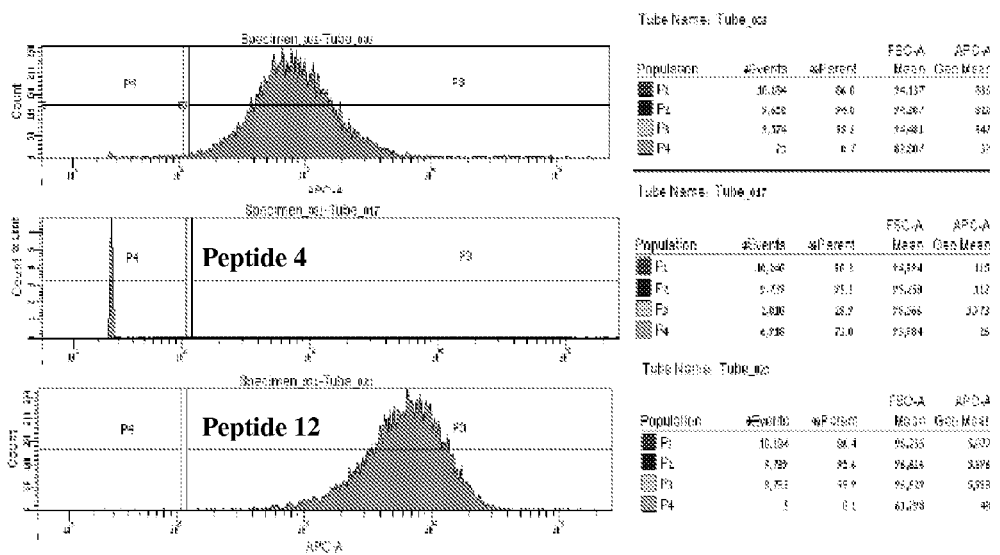
FIG. 4—Effect of peptides of SEQ ID NOS: 4 and 12 on NKp46D2-Ig staining of HeLa cells.
Figure 7:
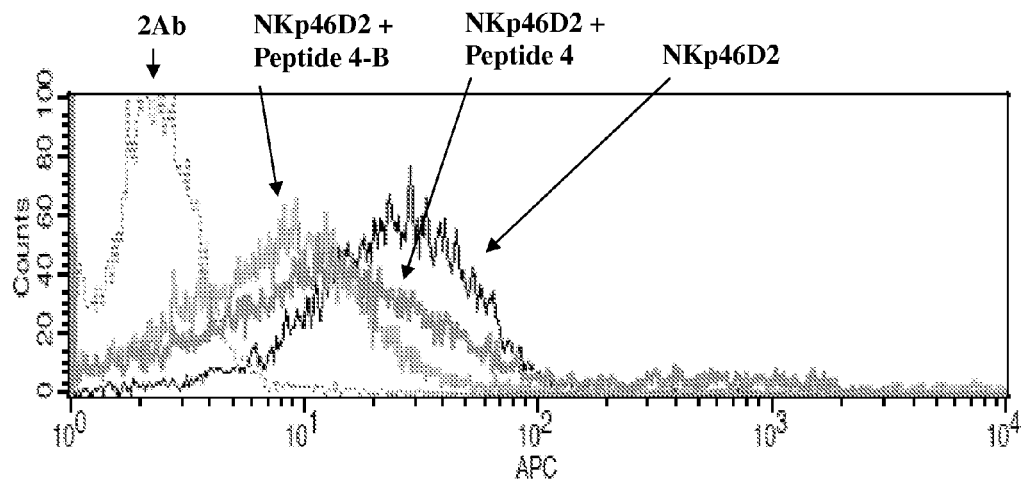
FIG. 7—Overlay of effects of NKp46-derived peptide 4 on NKp46D2-Ig binding to HeLa cells. The term "-B" means biotin added at N-terminus; "2Ab" shows staining only with 2nd reagent (goat anti-human Fcγ); and "NKp46D2" shows staining only with NKp46D2-Ig.
Figure 8:
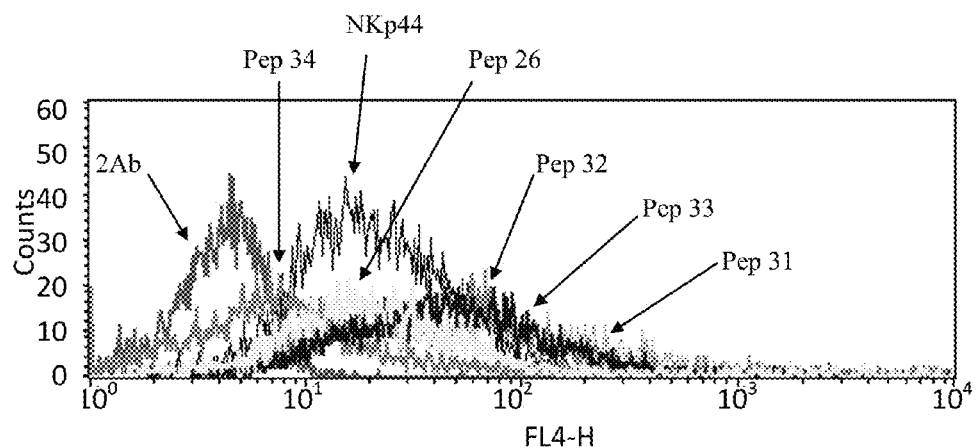
FIG. 8—Overlay of effects of NKp44-derived peptides 26, 31, 32, 33 and 34 on NKp44-Ig binding to HeLa cells.

Binding to Target Cells (A) Peptides of SEQ ID NOS: 4, 5 and 6 each exhibited activity in inhibiting binding of NKp46D2-Ig to target cell populations, as compared to NKp46D2-Ig staining without peptide or with non-affecting peptides (FIGS. 4 and 7).

Figure 6:
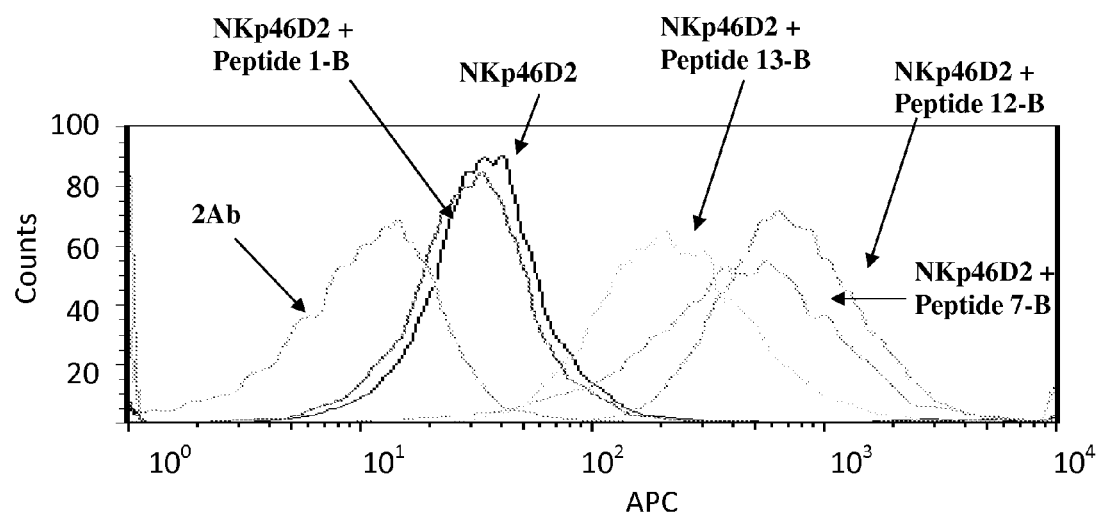
FIG. 6—Overlay of effects of NKp46D2-derived peptides 7, 12 and 13 on NKp46D2-Ig binding to HeLa cells. NKp46-derived peptide 1 (SEQ ID NO: 1) was used as a control peptide. The term "-B" means biotin added at N-terminus; "2Ab" shows staining only with 2nd reagent (goat anti-human Fcγ); and "NKp46D2" shows staining only with NKp46D2-Ig.

Peptides of SEQ ID NOS: 7, 12 and 13 each exhibited activity in enhancing NKp46D2-Ig binding to target cell populations, as compared to NKp46D2-Ig staining without peptide or with non-affecting peptides (FIGS. 2, 4 and 6).

Figure 3:
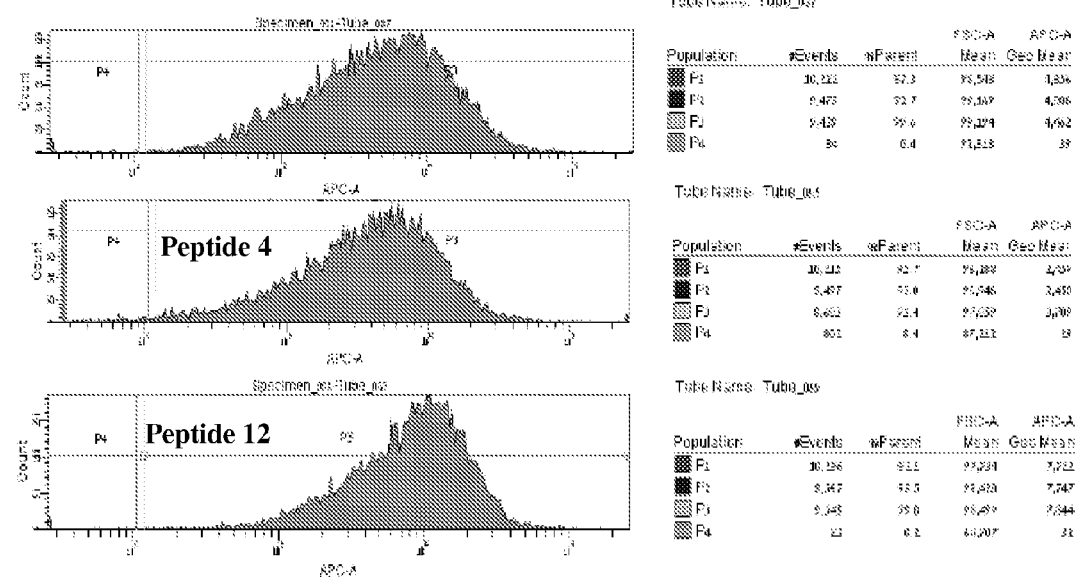
FIG. 3—Effect of peptides of SEQ ID NOS: 4 and 12 on LIR-Ig staining of HeLa cells.
Figure 5:
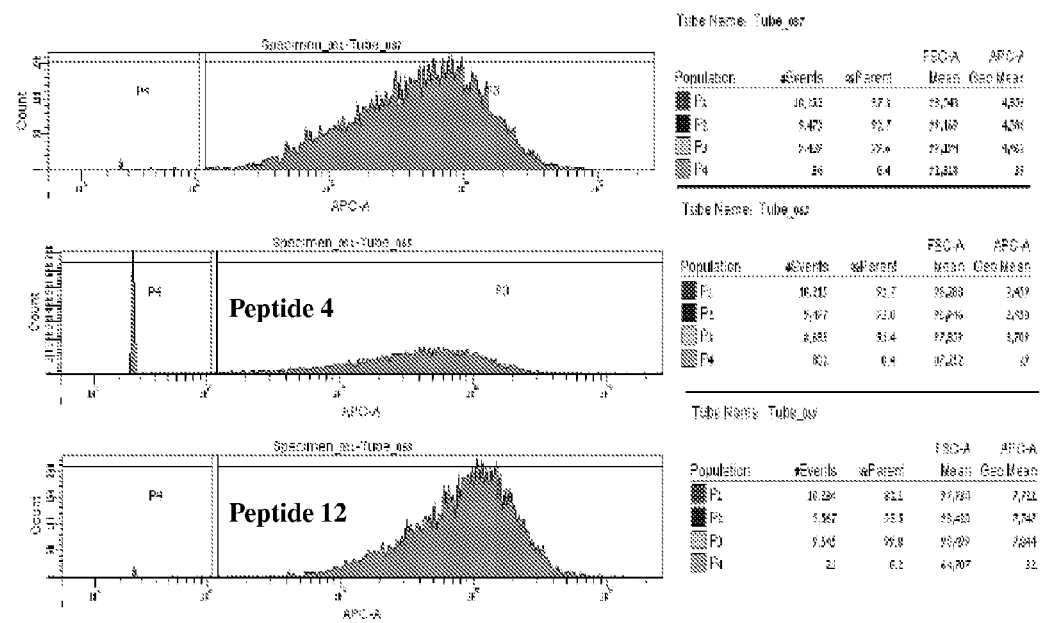
FIG. 5—Effect of peptides of SEQ ID NOS: 4 and 12 on LIR-Ig staining of HeLa cells.

(B) The binding of another recombinant NK receptor fusion protein, LIR1-Ig, was not affected in the presence of any of the NKp46 affecting peptides (SEQ ID NOS: 4, 5, 6, 7, 12 and 13; see FIGS. 3 and 5).

(C) Peptides of SEQ ID NOS: 7, 12 and 13 each exhibited direct binding to target cells.

The results are summarized in Table 1. Essential amino acids are underlined.

TABLE 1

NKp46-derived peptides and effect.

| Peptide Sequence No. | Sequence | Direct binding to cells | Effect on NKp46D2L binding to cells |
|---|---|---|---|
| 4 | SGEKV TFYC<u>R</u> L<u>D</u>TAT SMFLL | No | Suppress (2) |
| 5 | TFYC<u>R</u> L<u>D</u>TAT SMFLL LKEGR | No | Suppress (2) |
| 6 | L<u>D</u>TAT SMFLL LKEGR SSHVQ | No | Suppress (1) |
| 7 | S<u>MFLL</u> L<u>K</u>EGR SS<u>H</u>VQ <u>R</u>GYG<u>K</u> | Yes (1) | Enhance (2) |
| 12 | PLGPV TTA<u>HR</u> GTYRC FGSYN | Yes (3) | Enhance (3) |
| 13 | TTA<u>HR</u> GTYRC FGSYN NHAWS | Yes (2) | Enhance (1.5) |

Effect on NK Function:

Peptide of SEQ ID NO: 4 was tested and found to inhibit lysis of target cells by NKp46-expressing NK cells.

Example 2

Isolated Peptides Derived from the Sequence of NKp44 and Activity Thereof

The ectodomain of NKp44 was devised into a series of 20 overlapping peptides, each 20 amino acids in length with an overlap region of 15 amino acids. The constructed peptides correspond to SEQ ID NOS: 25-44.

The peptides were tested for: (i) direct binding to human cancer cells; (ii) effect on binding of the fusion protein NKp44D-Ig (SEQ ID NO: 54) to human cancer cells.

Protocol

Target cells were incubated for 1.5 hr with 2 μg/well NKp44-Ig and 10 μg/well of each peptide. NKp44-Ig binding intensity was determined by flow cytometry, using fluorescent 2Ab (goat anti-mouse mAb). Biotin-conjugated peptides were employed separately (10 μg/well at 100 μl) to test for direct binding of the peptide to cells using fluorescent Streptavidin as the second step.

Results

Binding to Target Cells (A) Peptide of SEQ ID NO: 34 exhibited activity in inhibiting binding of NKp44D-Ig binding to target cell population, as compared to NKp44D-Ig staining without peptide or with non-affecting peptides.

(B) Peptides of SEQ ID NOS: 31-33 each exhibited activity in enhancing binding of NKp44D-Ig to target cell population, as compared to NKp44D-Ig staining without peptide or with non-affecting peptides.

(C) Peptides of SEQ ID NOS: 31-33 each showed direct binding to target cells.

The results are summarized in Table 2.

TABLE 2

NKp44-derived peptides and effect.

| Peptide SEQ ID No. | Sequence | Direct binding to tumor cells | Effect on NKp44-Ig binding to tumor cells |
|---|---|---|---|
| 31 | KGWCKEASALVCIRLVTSSK | Yes (1) | Enhance (1) |
| 32 | EASALVCIRLVTSSKPRTVA | Yes (1) | Enhance (1) |
| 33 | VCIRLVTSSKPRTMAWTSRF | (+/-) | Enhance (1) |
| 34 | VTSSKPRTMAWTSRFTIWD | No | Suppress (1.5) |

Example 3

The Effect of NKp46-derived Peptides on the Binding of Recombinant NKp46 to Tumor Cells Protocol Target cells were stained with 2 μg/well of NK receptor-Igs in the presence of 10 μg/well of SEQ ID NO: 4, 5, 55 (15mer-shared core sequence between SEQ ID NO:4 and 5), or SEQ ID NO: 1. The NK receptor-Ig staining intensities were determined by flow cytometry, using fluorescent APC-conjugated F(ab')$_2$ goat anti-human IgG.

Results

Figure 9A:
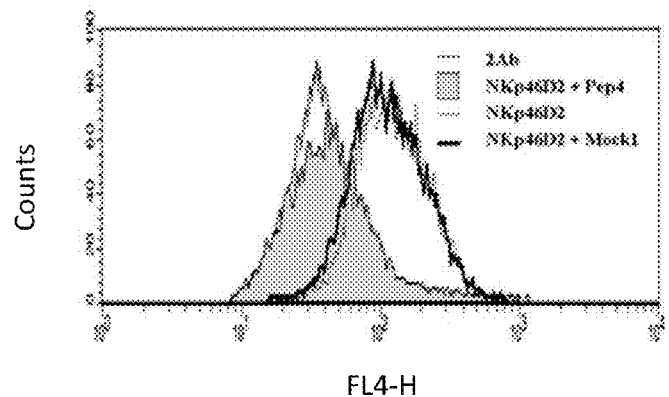
FIG. 9A-9D—Effect of peptides of SEQ ID NO: 4, 5 and 55 on binding of rNKp46 to target cells. The NK receptor-Ig staining intensities were determined by flow cytometry, using fluorescent APC-conjugated F(ab')2 goat anti-human IgG.

FIG. 9A shows that the peptide of SEQ ID NO: 4 (denoted pep4) inhibited binding upon co-incubation with NKp46D2-Ig (FIG. 9A). Similar results were demonstrated for the peptide of SEQ ID NO: 5 (denoted pep5). As NKp46-derived control peptides, the two ends of the 24 overlapping peptides were used, SEQ ID NO: 1 (denoted mock1) and SEQ ID NO: 24 (denoted mock2).

Figure 9B:
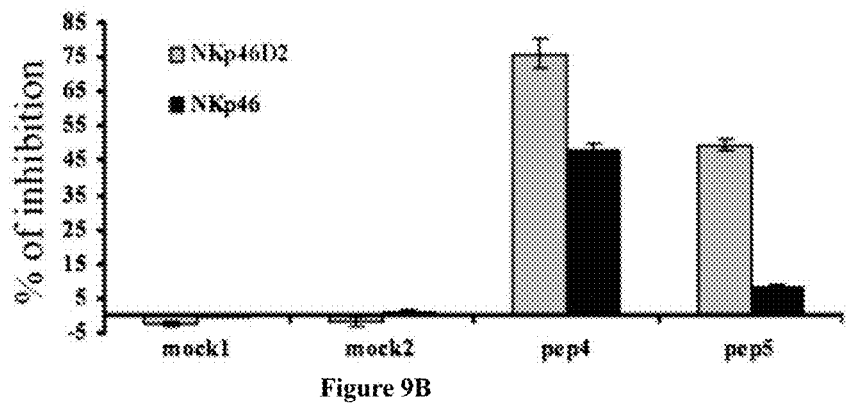

NKp46-Ig binding was also inhibited by the peptides of SEQ ID NO: 4 and SEQ ID NO: 5, yet to a lesser extent than the binding of NKp46D2-Ig (FIG. 9B). SEQ ID NOs: 4 and 5 overlap and in accordance, SEQ ID NO: 55 (the 15mer-shared core sequence) also inhibited NKp46-Ig binding to tumor cells (FIG. 9C).

Figure 9C:
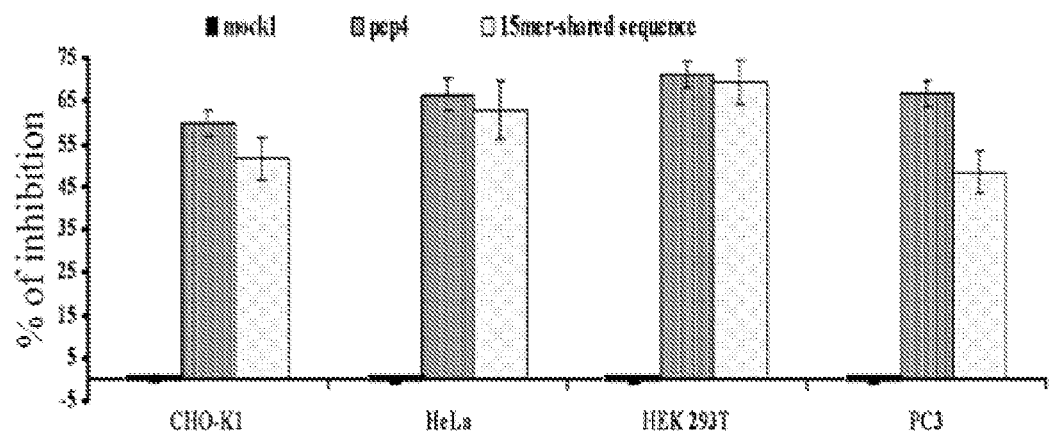
Figure 9D:
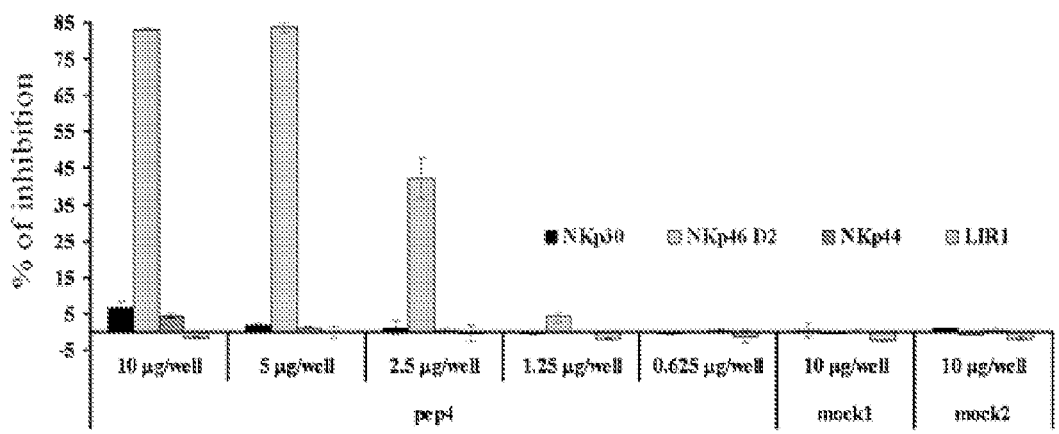

The mediated inhibition of the peptide of SEQ ID NO: 4 on rNKp46 binding was evident for numerous tumor cell lines from human (HeLa, PC-3, HEK293T, 721.221) and non human (CHO-K1 and MIN-6) origin (FIG. 9C). This is in accordance with evidence that human NKp46 recognizes ligands on human and non-human tumor cell lines. The binding inhibition was specific to NKp46 since the peptide of SEQ ID NO: 4 did not induce significant binding inhibition for other NK receptor-Igs such as NKp30-Ig, NKp44-Ig and LIR1-Ig (FIG. 9D).

Example 3 shows that NKp46-derived peptides, particularly the peptide of SEQ ID NO: 4, 5 and 55 inhibit the binding of recombinant NKp46 to tumor cells.

Example 4

Figure 10A:
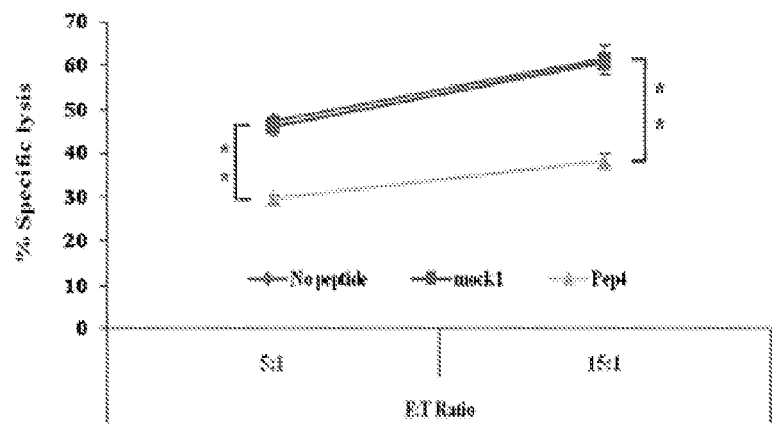
FIG. 10A-10C—Effect of the peptide of SEQ ID NO: 4 on target cells lysis and CD107a (LAMP-1) expression on primary NK cells.
Figure 10B:
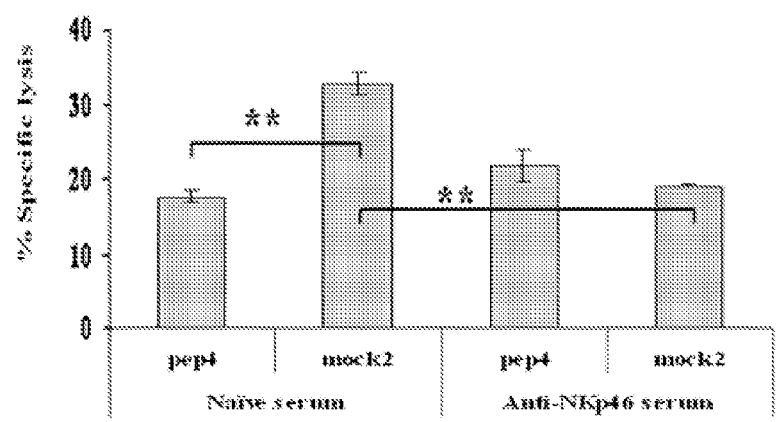

The Effect of NKp46-derived Peptides on the NK Degranulation and Lysis of Tumor Cells Next, the influence of the peptide of SEQ ID NO: 4 on NK cells function was investigated. Target HeLa cells were plated and pep4 or mock peptide was added just before adding an effector human primary NK cell line. Lysis of target cells was significantly suppressed when the peptide of SEQ ID NO: 4 was added, as compared to control (mock1; FIG. 10A, p<0.01). Similarly, the pep4-mediated inhibition of lysis was obtained for target 721.221 and CHO-K1 cells. To verify that the peptide of SEQ ID NO: 4 inhibits NKp46-mediated lysis, anti-NKp46 serum was used to block the receptor on human primary NK cells. As above, in the presence of only control serum, the peptide of SEQ ID NO: 4 inhibited lysis, as compared to the control peptide (FIG. 10B, p<0.01). The lysis of target cells was mediated by NKp46; incubation with anti-NKp46 serum and mock peptide significantly reduced lysis of target cells by effector NK cells, as compared to incubation with control serum and control peptide. In contrast, when the peptide of SEQ ID NO: 4 was present, no blocking effect was observed for anti-NKp46 serum as compared to control serum (FIG. 10B). Therefore, the inhibition of lysis mediated by the peptide of SEQ ID NO: 4 involves the NKp46 receptor.

Figure 10C:
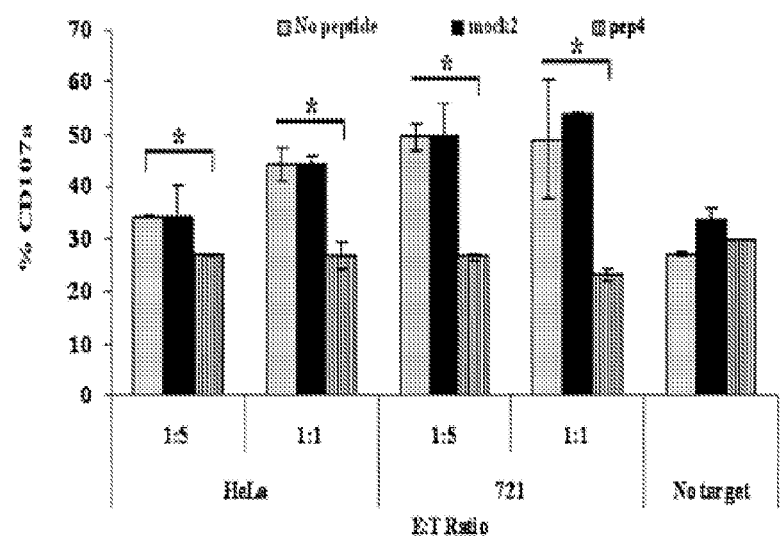
Figure 11D:
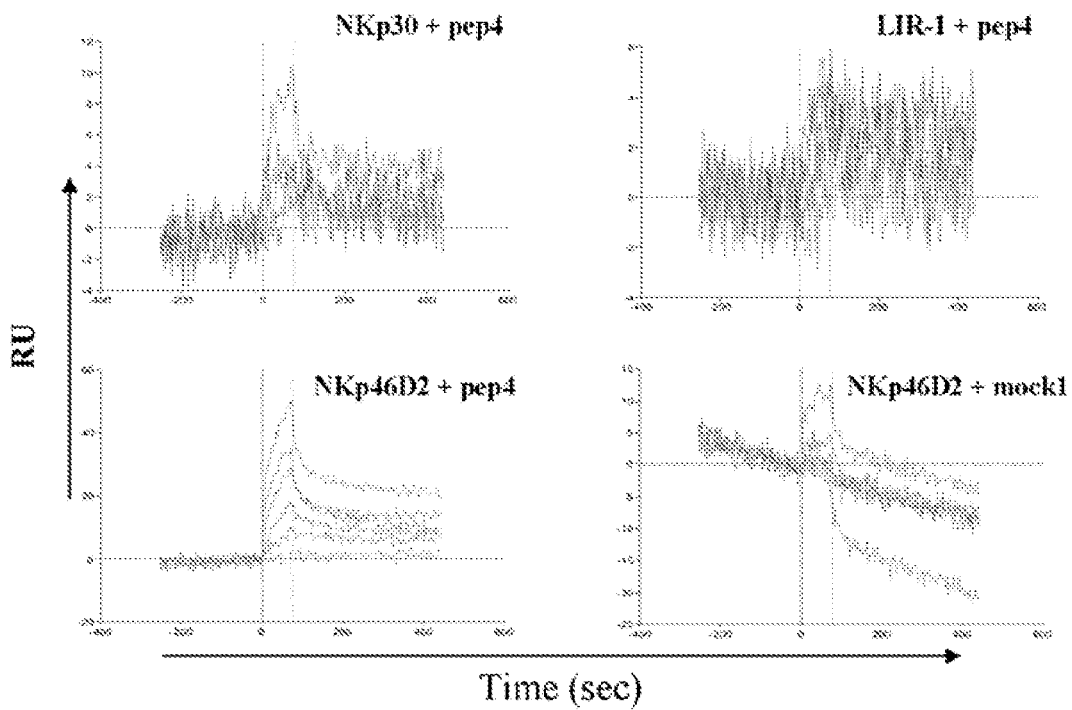
Figure 11E:
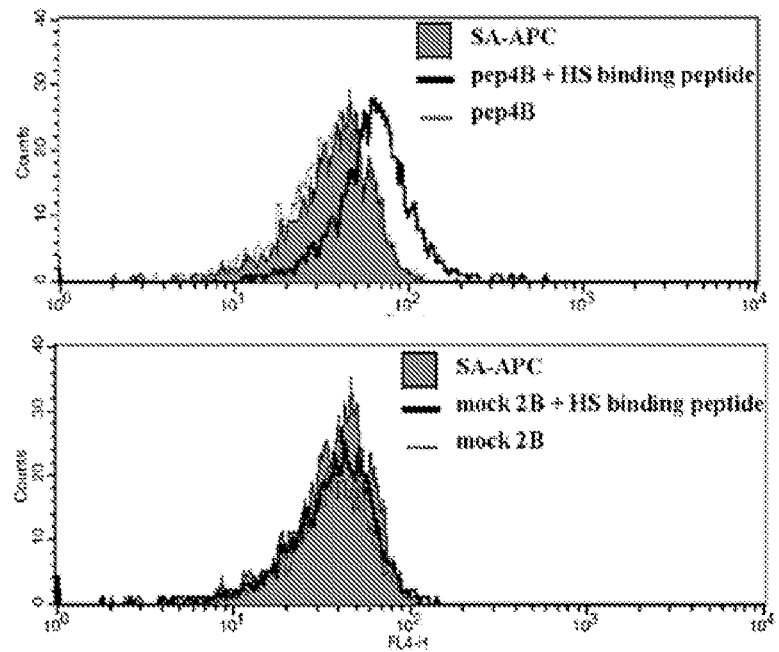
Figure 12:
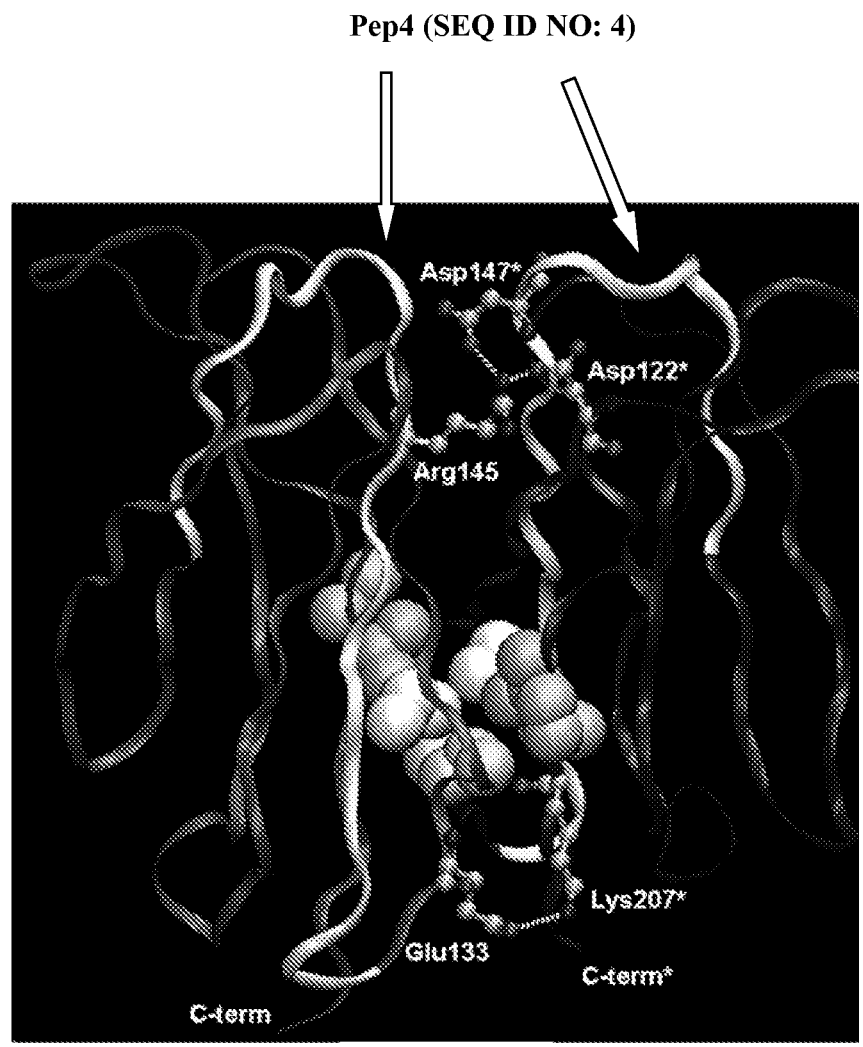
Figure 14A:
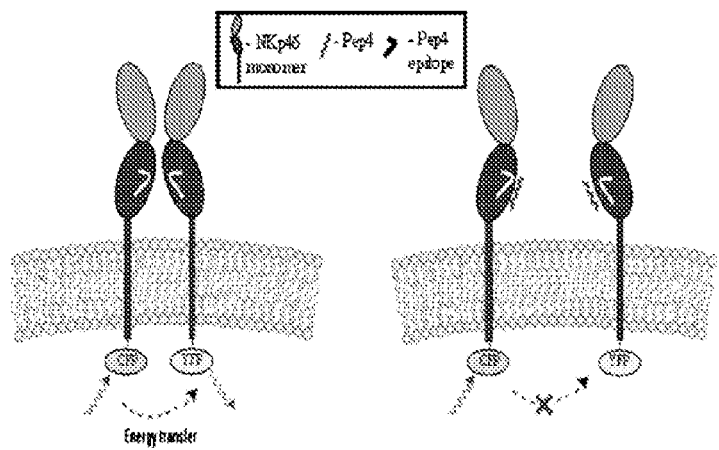
Figure 14B:
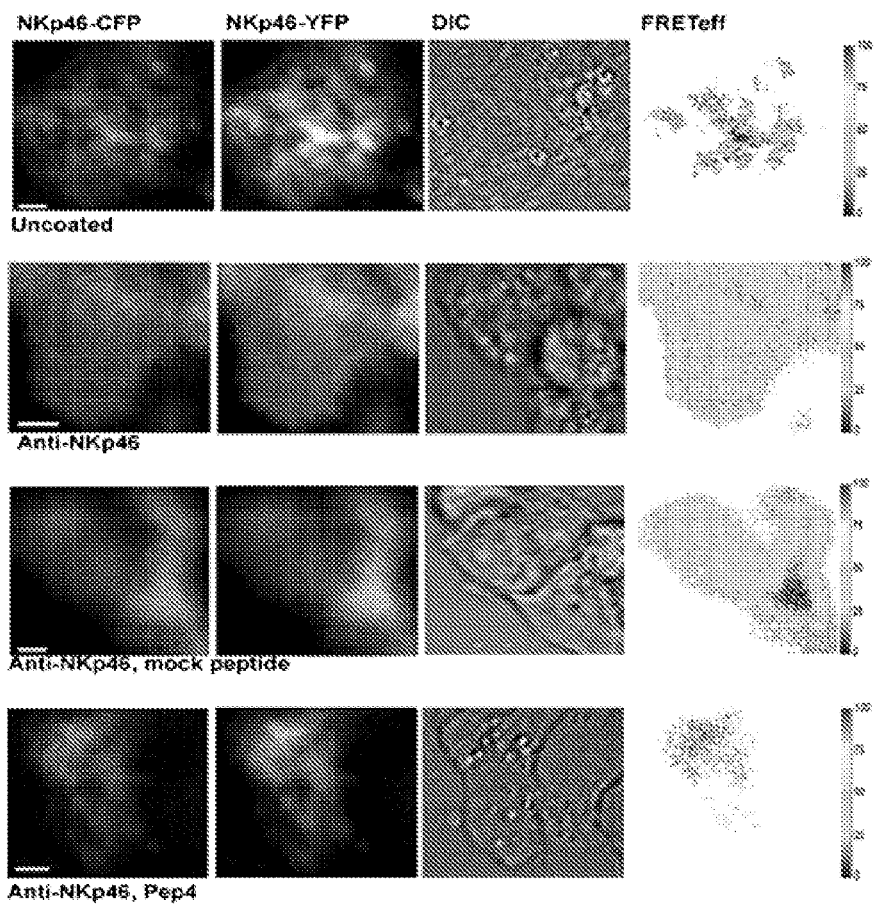
Figure 14C:
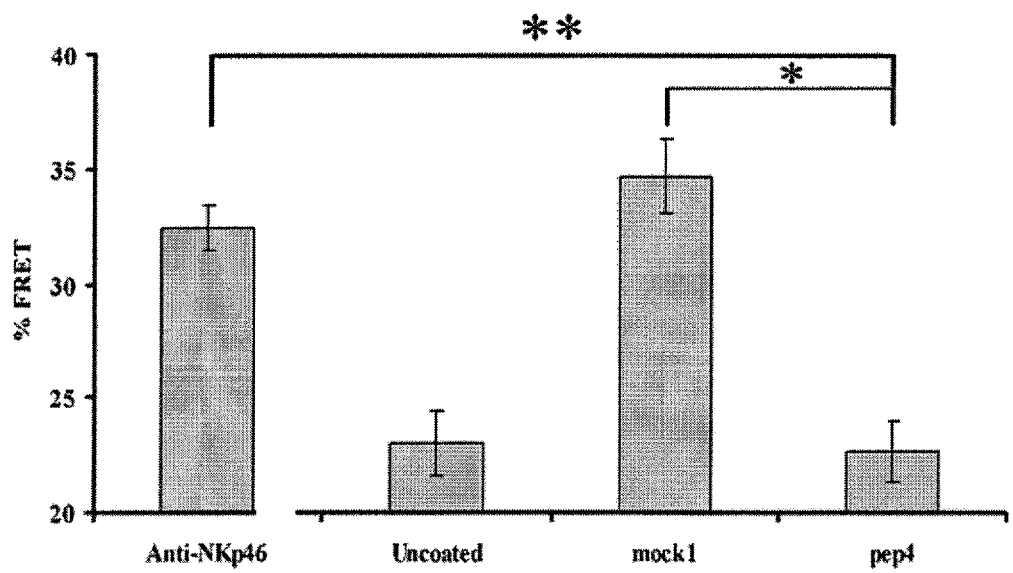
Figure 14D:
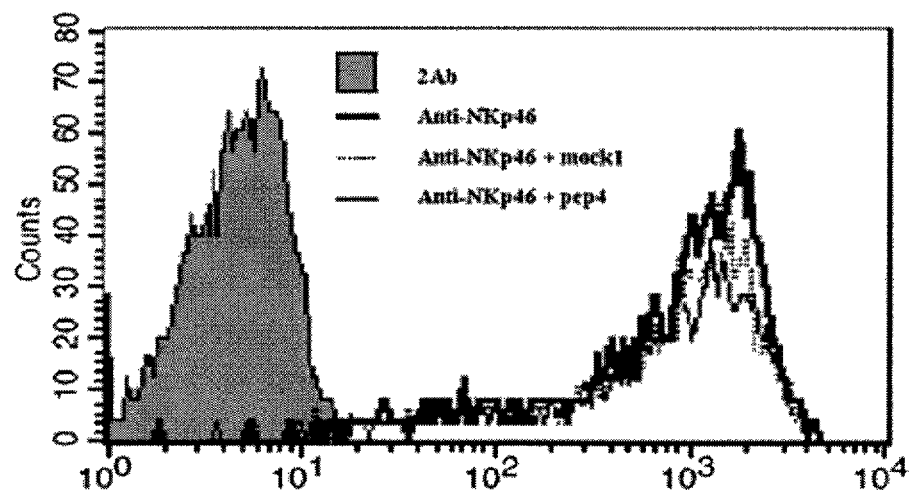

To further assess the influence of the peptide of SEQ ID NO: 4 on NK activation, human primary NK cell line were stained for CD107a (LAMP-1) cell surface expression, which is a marker for NK cell degranulation and functional activity. NK cells and HeLa or 721.221 target cells were co-cultured for four hours at different E:T ratios in the presence of the peptide of SEQ ID NO: 4 or a control peptide. The percentage of CD107a$^+$ NK cells was significantly reduced when co-cultured with target cells in the presence of the peptide of SEQ ID NO: 4 (FIG. 10C, p<0.05).

Example 4 shows that the peptide of SEQ ID NO: 4 inhibits NK degranulation and lysis of tumor cells.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An isolated peptide of 10 to 30 amino acid residues in length comprising a fragment of the ectodomain of the cytotoxicity receptor natural killer protein 44 (NKp44), the peptide comprising the amino acid sequence selected from the group consisting of: SEQ ID NOS: 31-33, or a fragment thereof comprising at least 10 contiguous amino acids.

2. The peptide according to claim 1, wherein the NKp44 is a human natural cytotoxicity receptor protein.

3. The peptide according to claim 1, wherein the ectodomain of NKp44 comprises SEQ ID NO: 51.

4. The peptide according to claim 1, wherein said peptide consists of the amino acid sequence selected from the group consisting of: SEQ ID NOS: 31, 32, and 33.

5. The isolated peptide according to claim 1 which corresponds to a fragment of the ectodomain of the natural cytotoxicity receptor protein NKp44, the peptide comprising the amino acid sequence selected from the group consisting of: SEQ ID NO: 59 (VCIRLVTSSK) and SEQ ID NO: 60 (VTSSKPRTXA), wherein X in SEQ ID NO: 60 denotes V or M.

6. The isolated peptide according to claim 1 which corresponds to a fragment of the ectodomain of the natural cytotoxicity receptor protein NKp44, the peptide comprising the amino acid sequence set forth in SEQ ID NO: 61 (VCIRLVTSSKPRTXA), wherein X in SEQ ID NO: 61 denotes V or M.

7. A pharmaceutical composition comprising the isolated peptide of claim 1 and a pharmaceutically acceptable carrier.

8. A fusion protein or chimeric peptide comprising the isolated peptide of claim 1.

9. A method for treating cancer, the method comprising administering to a subject in need thereof a pharmaceutical composition comprising a therapeutically effective amount of an isolated peptide of 10 to 30 amino acid residues in length comprising a fragment of the ectodomain of the cytotoxicity receptor natural killer protein 44 (NKp44); wherein the peptide comprise the amino acid sequence selected from the group consisting of SEQ ID NOS: 31-33, or a fragment thereof comprising at least 10 contiguous amino acids, thereby treating cancer in the subject, wherein the cancer is one selected from the group consisting of hematologic cancers, bladder cancer, bone cancer, breast cancer, cervical cancer, colon cancer, endometrial cancer, gastric cancer, head and neck cancer, hepatic cancer, kidney cancer, lung cancer, melanoma, ovarian cancer, pancreatic cancer, prostate cancer, renal cancer, sarcoma, skin cancer, stomach cancer, testicular cancer and thyroid cancer.

10. The method according to claim 9, wherein the peptide consists of an amino acid sequence selected from the group consisting of SEQ ID NOS: 31, 32, and 33.

11. The method according to claim 9, wherein the administering is carried out by a route selected from the group consisting of parenteral, oral and transdermal.

12. The method according to claim 9, wherein NKp44 is a human natural cytotoxicity receptor protein.

13. The method according to claim 9, wherein the peptide comprises an amino acid sequence selected from the group consisting of SEQ ID NOS: 59-61, wherein X in SEQ ID NOS: 60 and 61 denotes V or M.

14. The method according to claim 9, wherein the pharmaceutical composition further comprising a pharmaceutically acceptable carrier.

* * * * *

```
                          SEQUENCE LISTING

<160> NUMBER OF SEQ ID NOS: 61

<210> SEQ ID NO 1
<211> LENGTH: 20
<212> TYPE: PRT
<213> ORGANISM: Artificial
<220> FEATURE:
<223> OTHER INFORMATION: Synthetic peptide

<400> SEQUENCE: 1

Tyr Asp Thr Pro Thr Leu Ser Val His Pro Gly Pro Glu Val Ile Ser
1               5                   10                  15

Gly Glu Lys Val
            20

<210> SEQ ID NO 2
<211> LENGTH: 20
<212> TYPE: PRT
<213> ORGANISM: Artificial
<220> FEATURE:
<223> OTHER INFORMATION: Synthetic peptide

<400> SEQUENCE: 2

Leu Ser Val His Pro Gly Pro Glu Val Ile Ser Gly Glu Lys Val Thr
1               5                   10                  15

Phe Tyr Cys Arg
            20

<210> SEQ ID NO 3
<211> LENGTH: 20
<212> TYPE: PRT
<213> ORGANISM: Artificial
<220> FEATURE:
<223> OTHER INFORMATION: Synthetic peptide

<400> SEQUENCE: 3

Gly Pro Glu Val Ile Ser Gly Glu Lys Val Thr Phe Tyr Cys Arg Leu
1               5                   10                  15

Asp Thr Ala Thr
            20

<210> SEQ ID NO 4
<211> LENGTH: 20
<212> TYPE: PRT
<213> ORGANISM: Artificial
<220> FEATURE:
<223> OTHER INFORMATION: Synthetic peptide

<400> SEQUENCE: 4

Ser Gly Glu Lys Val Thr Phe Tyr Cys Arg Leu Asp Thr Ala Thr Ser
1               5                   10                  15

Met Phe Leu Leu
            20

<210> SEQ ID NO 5
<211> LENGTH: 20
<212> TYPE: PRT
<213> ORGANISM: Artificial
```

```
<220> FEATURE:
<223> OTHER INFORMATION: Synthetic peptide

<400> SEQUENCE: 5

Thr Phe Tyr Cys Arg Leu Asp Thr Ala Thr Ser Met Phe Leu Leu Leu
1               5                   10                  15

Lys Glu Gly Arg
            20

<210> SEQ ID NO 6
<211> LENGTH: 20
<212> TYPE: PRT
<213> ORGANISM: Artificial
<220> FEATURE:
<223> OTHER INFORMATION: Synthetic peptide

<400> SEQUENCE: 6

Leu Asp Thr Ala Thr Ser Met Phe Leu Leu Leu Lys Glu Gly Arg Ser
1               5                   10                  15

Ser His Val Gln
            20

<210> SEQ ID NO 7
<211> LENGTH: 20
<212> TYPE: PRT
<213> ORGANISM: Artificial
<220> FEATURE:
<223> OTHER INFORMATION: Synthetic peptide

<400> SEQUENCE: 7

Ser Met Phe Leu Leu Leu Lys Glu Gly Arg Ser Ser His Val Gln Arg
1               5                   10                  15

Gly Tyr Gly Lys
            20

<210> SEQ ID NO 8
<211> LENGTH: 20
<212> TYPE: PRT
<213> ORGANISM: Artificial
<220> FEATURE:
<223> OTHER INFORMATION: Synthetic peptide

<400> SEQUENCE: 8

Leu Lys Glu Gly Arg Ser Ser His Val Gln Arg Gly Tyr Gly Lys Val
1               5                   10                  15

Gln Ala Glu Phe
            20

<210> SEQ ID NO 9
<211> LENGTH: 20
<212> TYPE: PRT
<213> ORGANISM: Artificial
<220> FEATURE:
<223> OTHER INFORMATION: Synthetic peptide

<400> SEQUENCE: 9

Ser Ser His Val Gln Arg Gly Tyr Gly Lys Val Gln Ala Glu Phe Pro
1               5                   10                  15

Leu Gly Pro Val
            20

<210> SEQ ID NO 10
<211> LENGTH: 20
<212> TYPE: PRT
```

```
<213> ORGANISM: Artificial
<220> FEATURE:
<223> OTHER INFORMATION: Synthetic peptide

<400> SEQUENCE: 10

Arg Gly Tyr Gly Lys Val Gln Ala Glu Phe Pro Leu Gly Pro Val Thr
1               5                   10                  15

Thr Ala His Arg
            20

<210> SEQ ID NO 11
<211> LENGTH: 20
<212> TYPE: PRT
<213> ORGANISM: Artificial
<220> FEATURE:
<223> OTHER INFORMATION: Synthetic peptide

<400> SEQUENCE: 11

Val Gln Ala Glu Phe Pro Leu Gly Pro Val Thr Thr Ala His Arg Gly
1               5                   10                  15

Thr Tyr Arg Cys
            20

<210> SEQ ID NO 12
<211> LENGTH: 20
<212> TYPE: PRT
<213> ORGANISM: Artificial
<220> FEATURE:
<223> OTHER INFORMATION: Synthetic peptide

<400> SEQUENCE: 12

Pro Leu Gly Pro Val Thr Thr Ala His Arg Gly Thr Tyr Arg Cys Phe
1               5                   10                  15

Gly Ser Tyr Asn
            20

<210> SEQ ID NO 13
<211> LENGTH: 20
<212> TYPE: PRT
<213> ORGANISM: Artificial
<220> FEATURE:
<223> OTHER INFORMATION: Synthetic peptide

<400> SEQUENCE: 13

Thr Thr Ala His Arg Gly Thr Tyr Arg Cys Phe Gly Ser Tyr Asn Asn
1               5                   10                  15

His Ala Trp Ser
            20

<210> SEQ ID NO 14
<211> LENGTH: 20
<212> TYPE: PRT
<213> ORGANISM: Artificial
<220> FEATURE:
<223> OTHER INFORMATION: Synthetic peptide

<400> SEQUENCE: 14

Gly Thr Tyr Arg Cys Phe Gly Ser Tyr Asn Asn His Ala Trp Ser Phe
1               5                   10                  15

Pro Ser Glu Pro
            20

<210> SEQ ID NO 15
<211> LENGTH: 20
```

```
<212> TYPE: PRT
<213> ORGANISM: Artificial
<220> FEATURE:
<223> OTHER INFORMATION: Synthetic peptide

<400> SEQUENCE: 15

Phe Gly Ser Tyr Asn Asn His Ala Trp Ser Phe Pro Ser Glu Pro Val
1               5                   10                  15

Lys Leu Leu Val
            20

<210> SEQ ID NO 16
<211> LENGTH: 20
<212> TYPE: PRT
<213> ORGANISM: Artificial
<220> FEATURE:
<223> OTHER INFORMATION: Synthetic peptide

<400> SEQUENCE: 16

Asn His Ala Trp Ser Phe Pro Ser Glu Pro Val Lys Leu Leu Val Thr
1               5                   10                  15

Gly Asp Ile Glu
            20

<210> SEQ ID NO 17
<211> LENGTH: 20
<212> TYPE: PRT
<213> ORGANISM: Artificial
<220> FEATURE:
<223> OTHER INFORMATION: Synthetic peptide

<400> SEQUENCE: 17

Phe Pro Ser Glu Pro Val Lys Leu Leu Val Thr Gly Asp Ile Glu Asn
1               5                   10                  15

Thr Ser Leu Ala
            20

<210> SEQ ID NO 18
<211> LENGTH: 20
<212> TYPE: PRT
<213> ORGANISM: Artificial
<220> FEATURE:
<223> OTHER INFORMATION: Synthetic peptide

<400> SEQUENCE: 18

Val Lys Leu Leu Val Thr Gly Asp Ile Glu Asn Thr Ser Leu Ala Pro
1               5                   10                  15

Glu Asp Pro Thr
            20

<210> SEQ ID NO 19
<211> LENGTH: 20
<212> TYPE: PRT
<213> ORGANISM: Artificial
<220> FEATURE:
<223> OTHER INFORMATION: Synthetic peptide

<400> SEQUENCE: 19

Thr Gly Asp Ile Glu Asn Thr Ser Leu Ala Pro Glu Asp Pro Thr Phe
1               5                   10                  15

Pro Ala Asp Thr
            20

<210> SEQ ID NO 20
```

```
<211> LENGTH: 20
<212> TYPE: PRT
<213> ORGANISM: Artificial
<220> FEATURE:
<223> OTHER INFORMATION: Synthetic peptide

<400> SEQUENCE: 20

Asn Thr Ser Leu Ala Pro Glu Asp Pro Thr Phe Pro Ala Asp Thr Trp
1               5                   10                  15

Gly Thr Tyr Leu
            20

<210> SEQ ID NO 21
<211> LENGTH: 20
<212> TYPE: PRT
<213> ORGANISM: Artificial
<220> FEATURE:
<223> OTHER INFORMATION: Synthetic peptide

<400> SEQUENCE: 21

Pro Glu Asp Pro Thr Phe Pro Ala Asp Thr Trp Gly Thr Tyr Leu Leu
1               5                   10                  15

Thr Thr Glu Thr
            20

<210> SEQ ID NO 22
<211> LENGTH: 20
<212> TYPE: PRT
<213> ORGANISM: Artificial
<220> FEATURE:
<223> OTHER INFORMATION: Synthetic peptide

<400> SEQUENCE: 22

Phe Pro Ala Asp Thr Trp Gly Thr Tyr Leu Leu Thr Thr Glu Thr Gly
1               5                   10                  15

Leu Gln Lys Asp
            20

<210> SEQ ID NO 23
<211> LENGTH: 20
<212> TYPE: PRT
<213> ORGANISM: Artificial
<220> FEATURE:
<223> OTHER INFORMATION: Synthetic peptide

<400> SEQUENCE: 23

Trp Gly Thr Tyr Leu Leu Thr Thr Glu Thr Gly Leu Gln Lys Asp His
1               5                   10                  15

Ala Leu Trp Asp
            20

<210> SEQ ID NO 24
<211> LENGTH: 19
<212> TYPE: PRT
<213> ORGANISM: Artificial
<220> FEATURE:
<223> OTHER INFORMATION: Synthetic peptide

<400> SEQUENCE: 24

Leu Thr Thr Glu Thr Gly Leu Gln Lys Asp His Ala Leu Trp Asp His
1               5                   10                  15

Thr Ala Gln

<210> SEQ ID NO 25
```

<211> LENGTH: 20
<212> TYPE: PRT
<213> ORGANISM: Artificial
<220> FEATURE:
<223> OTHER INFORMATION: Synthetic peptide

<400> SEQUENCE: 25

Gln Ser Lys Ala Gln Val Leu Gln Ser Val Ala Gly Gln Thr Leu Thr
1               5                   10                  15
Val Arg Cys Gln
            20

<210> SEQ ID NO 26
<211> LENGTH: 20
<212> TYPE: PRT
<213> ORGANISM: Artificial
<220> FEATURE:
<223> OTHER INFORMATION: Synthetic peptide

<400> SEQUENCE: 26

Val Leu Gln Ser Val Ala Gly Gln Thr Leu Thr Val Arg Cys Gln Tyr
1               5                   10                  15
Pro Pro Thr Gly
            20

<210> SEQ ID NO 27
<211> LENGTH: 20
<212> TYPE: PRT
<213> ORGANISM: Artificial
<220> FEATURE:
<223> OTHER INFORMATION: Synthetic peptide

<400> SEQUENCE: 27

Ala Gly Gln Thr Leu Thr Val Arg Cys Gln Tyr Pro Pro Thr Gly Ser
1               5                   10                  15
Leu Tyr Glu Lys
            20

<210> SEQ ID NO 28
<211> LENGTH: 20
<212> TYPE: PRT
<213> ORGANISM: Artificial
<220> FEATURE:
<223> OTHER INFORMATION: Synthetic peptide

<400> SEQUENCE: 28

Thr Val Arg Cys Gln Tyr Pro Pro Thr Gly Ser Leu Tyr Glu Lys Lys
1               5                   10                  15
Gly Trp Cys Lys
            20

<210> SEQ ID NO 29
<211> LENGTH: 20
<212> TYPE: PRT
<213> ORGANISM: Artificial
<220> FEATURE:
<223> OTHER INFORMATION: Synthetic peptide

<400> SEQUENCE: 29

Tyr Pro Pro Thr Gly Ser Leu Tyr Glu Lys Lys Gly Trp Cys Lys Glu
1               5                   10                  15
Ala Ser Ala Leu
            20

```
<210> SEQ ID NO 30
<211> LENGTH: 20
<212> TYPE: PRT
<213> ORGANISM: Artificial
<220> FEATURE:
<223> OTHER INFORMATION: Synthetic peptide

<400> SEQUENCE: 30

Ser Leu Tyr Glu Lys Lys Gly Trp Cys Lys Glu Ala Ser Ala Leu Val
1               5                   10                  15

Cys Ile Arg Leu
            20

<210> SEQ ID NO 31
<211> LENGTH: 20
<212> TYPE: PRT
<213> ORGANISM: Artificial
<220> FEATURE:
<223> OTHER INFORMATION: Synthetic peptide

<400> SEQUENCE: 31

Lys Gly Trp Cys Lys Glu Ala Ser Ala Leu Val Cys Ile Arg Leu Val
1               5                   10                  15

Thr Ser Ser Lys
            20

<210> SEQ ID NO 32
<211> LENGTH: 20
<212> TYPE: PRT
<213> ORGANISM: Artificial
<220> FEATURE:
<223> OTHER INFORMATION: Synthetic peptide

<400> SEQUENCE: 32

Glu Ala Ser Ala Leu Val Cys Ile Arg Leu Val Thr Ser Ser Lys Pro
1               5                   10                  15

Arg Thr Val Ala
            20

<210> SEQ ID NO 33
<211> LENGTH: 20
<212> TYPE: PRT
<213> ORGANISM: Artificial
<220> FEATURE:
<223> OTHER INFORMATION: Synthetic peptide

<400> SEQUENCE: 33

Val Cys Ile Arg Leu Val Thr Ser Ser Lys Pro Arg Thr Met Ala Trp
1               5                   10                  15

Thr Ser Arg Phe
            20

<210> SEQ ID NO 34
<211> LENGTH: 20
<212> TYPE: PRT
<213> ORGANISM: Artificial
<220> FEATURE:
<223> OTHER INFORMATION: Synthetic peptide

<400> SEQUENCE: 34

Val Thr Ser Ser Lys Pro Arg Thr Val Ala Trp Thr Ser Arg Phe Thr
1               5                   10                  15

Ile Trp Asp Asp
            20
```

<210> SEQ ID NO 35
<211> LENGTH: 20
<212> TYPE: PRT
<213> ORGANISM: Artificial
<220> FEATURE:
<223> OTHER INFORMATION: Synthetic peptide

<400> SEQUENCE: 35

Pro Arg Thr Met Ala Trp Thr Ser Arg Phe Thr Ile Trp Asp Asp Pro
1               5                   10                  15
Asp Ala Gly Phe
            20

<210> SEQ ID NO 36
<211> LENGTH: 20
<212> TYPE: PRT
<213> ORGANISM: Artificial
<220> FEATURE:
<223> OTHER INFORMATION: Synthetic peptide

<400> SEQUENCE: 36

Trp Thr Ser Arg Phe Thr Ile Trp Asp Asp Pro Asp Ala Gly Phe Phe
1               5                   10                  15
Thr Val Thr Met
            20

<210> SEQ ID NO 37
<211> LENGTH: 20
<212> TYPE: PRT
<213> ORGANISM: Artificial
<220> FEATURE:
<223> OTHER INFORMATION: Synthetic peptide

<400> SEQUENCE: 37

Thr Ile Trp Asp Asp Pro Asp Ala Gly Phe Phe Thr Val Thr Met Thr
1               5                   10                  15
Asp Leu Arg Glu
            20

<210> SEQ ID NO 38
<211> LENGTH: 20
<212> TYPE: PRT
<213> ORGANISM: Artificial
<220> FEATURE:
<223> OTHER INFORMATION: Synthetic peptide

<400> SEQUENCE: 38

Pro Asp Ala Gly Phe Phe Thr Val Thr Met Thr Asp Leu Arg Glu Glu
1               5                   10                  15
Asp Ser Gly His
            20

<210> SEQ ID NO 39
<211> LENGTH: 20
<212> TYPE: PRT
<213> ORGANISM: Artificial
<220> FEATURE:
<223> OTHER INFORMATION: Synthetic peptide

<400> SEQUENCE: 39

Phe Thr Val Thr Met Thr Asp Leu Arg Glu Glu Asp Ser Gly His Tyr
1               5                   10                  15
Trp Cys Arg Ile
            20

<210> SEQ ID NO 40
<211> LENGTH: 20
<212> TYPE: PRT
<213> ORGANISM: Artificial
<220> FEATURE:
<223> OTHER INFORMATION: Synthetic peptide

<400> SEQUENCE: 40

Thr Asp Leu Arg Glu Glu Asp Ser Gly His Tyr Trp Cys Arg Ile Tyr
1               5                   10                  15

Arg Pro Ser Asp
            20

<210> SEQ ID NO 41
<211> LENGTH: 20
<212> TYPE: PRT
<213> ORGANISM: Artificial
<220> FEATURE:
<223> OTHER INFORMATION: Synthetic peptide

<400> SEQUENCE: 41

Glu Asp Ser Gly His Tyr Trp Cys Arg Ile Tyr Arg Pro Ser Asp Asn
1               5                   10                  15

Ser Val Ser Lys
            20

<210> SEQ ID NO 42
<211> LENGTH: 20
<212> TYPE: PRT
<213> ORGANISM: Artificial
<220> FEATURE:
<223> OTHER INFORMATION: Synthetic peptide

<400> SEQUENCE: 42

Tyr Trp Cys Arg Ile Tyr Arg Pro Ser Asp Asn Ser Val Ser Lys Ser
1               5                   10                  15

Val Arg Phe Tyr
            20

<210> SEQ ID NO 43
<211> LENGTH: 20
<212> TYPE: PRT
<213> ORGANISM: Artificial
<220> FEATURE:
<223> OTHER INFORMATION: Synthetic peptide

<400> SEQUENCE: 43

Tyr Arg Pro Ser Asp Asn Ser Val Ser Lys Ser Val Arg Phe Tyr Leu
1               5                   10                  15

Val Val Ser Pro
            20

<210> SEQ ID NO 44
<211> LENGTH: 20
<212> TYPE: PRT
<213> ORGANISM: Artificial
<220> FEATURE:
<223> OTHER INFORMATION: Synthetic peptide

<400> SEQUENCE: 44

His Tyr Trp Cys Arg Ile Tyr Arg Pro Ser Asp Asn Ser Val Ser Lys
1               5                   10                  15

Ser Val Arg Phe

-continued

20

<210> SEQ ID NO 45
<211> LENGTH: 134
<212> TYPE: PRT
<213> ORGANISM: Artificial
<220> FEATURE:
<223> OTHER INFORMATION: Synthetic peptide

<400> SEQUENCE: 45

Tyr Asp Thr Pro Thr Leu Ser Val His Pro Gly Pro Glu Val Ile Ser
1               5                  10                  15

Gly Glu Lys Val Thr Phe Tyr Cys Arg Leu Asp Thr Ala Thr Ser Met
            20                  25                  30

Phe Leu Leu Leu Lys Glu Gly Arg Ser Ser His Val Gln Arg Gly Tyr
        35                  40                  45

Gly Lys Val Gln Ala Glu Phe Pro Leu Gly Pro Val Thr Thr Ala His
    50                  55                  60

Arg Gly Thr Tyr Arg Cys Phe Gly Ser Tyr Asn Asn His Ala Trp Ser
65                  70                  75                  80

Phe Pro Ser Glu Pro Val Lys Leu Leu Val Thr Gly Asp Ile Glu Asn
                85                  90                  95

Thr Ser Leu Ala Pro Glu Asp Pro Thr Phe Pro Ala Asp Thr Trp Gly
            100                 105                 110

Thr Tyr Leu Leu Thr Thr Glu Thr Gly Leu Gln Lys Asp His Ala Leu
        115                 120                 125

Trp Asp His Thr Ala Gln
            130

<210> SEQ ID NO 46
<211> LENGTH: 117
<212> TYPE: PRT
<213> ORGANISM: Artificial
<220> FEATURE:
<223> OTHER INFORMATION: Synthetic peptide

<400> SEQUENCE: 46

Tyr Asp Thr Pro Thr Leu Ser Val His Pro Gly Pro Glu Val Ile Ser
1               5                  10                  15

Gly Glu Lys Val Thr Phe Tyr Cys Arg Leu Asp Thr Ala Thr Ser Met
            20                  25                  30

Phe Leu Leu Leu Lys Glu Gly Arg Ser Ser His Val Gln Arg Gly Tyr
        35                  40                  45

Gly Lys Val Gln Ala Glu Phe Pro Leu Gly Pro Val Thr Thr Ala His
    50                  55                  60

Arg Gly Thr Tyr Arg Cys Phe Gly Ser Tyr Asn Asn His Ala Trp Ser
65                  70                  75                  80

Phe Pro Ser Glu Pro Val Lys Leu Leu Val Thr Gly Asp Ile Glu Asn
                85                  90                  95

Thr Ser Leu Ala Pro Glu Asp Pro Thr Phe Pro Asp His Ala Leu Trp
            100                 105                 110

Asp His Thr Ala Gln
        115

<210> SEQ ID NO 47
<211> LENGTH: 134
<212> TYPE: PRT
<213> ORGANISM: Artificial
<220> FEATURE:

<223> OTHER INFORMATION: Synthetic peptide

<400> SEQUENCE: 47

Tyr Asp Thr Pro Thr Leu Ser Val His Pro Gly Pro Glu Val Ile Ser
1               5                   10                  15

Gly Glu Lys Val Thr Phe Tyr Cys Arg Leu Asp Thr Ala Thr Ser Met
            20                  25                  30

Phe Leu Leu Leu Lys Glu Gly Arg Ser Ser His Val Gln Arg Gly Tyr
        35                  40                  45

Gly Lys Val Gln Ala Glu Phe Pro Leu Gly Pro Val Thr Thr Ala His
    50                  55                  60

Arg Gly Thr Tyr Arg Cys Phe Gly Ser Tyr Asn Asn His Ala Trp Ser
65                  70                  75                  80

Phe Pro Ser Glu Pro Val Lys Leu Leu Val Thr Gly Asp Ile Glu Asn
                85                  90                  95

Thr Ser Leu Ala Pro Glu Asp Pro Thr Phe Pro Ala Asp Thr Trp Gly
            100                 105                 110

Thr Tyr Leu Leu Thr Thr Glu Thr Gly Leu Gln Lys Asp His Ala Leu
        115                 120                 125

Trp Asp His Thr Ala Gln
            130

<210> SEQ ID NO 48
<211> LENGTH: 117
<212> TYPE: PRT
<213> ORGANISM: Artificial
<220> FEATURE:
<223> OTHER INFORMATION: Synthetic peptide

<400> SEQUENCE: 48

Tyr Asp Thr Pro Thr Leu Ser Val His Pro Gly Pro Glu Val Ile Ser
1               5                   10                  15

Gly Glu Lys Val Thr Phe Tyr Cys Arg Leu Asp Thr Ala Thr Ser Met
            20                  25                  30

Phe Leu Leu Leu Lys Glu Gly Arg Ser Ser His Val Gln Arg Gly Tyr
        35                  40                  45

Gly Lys Val Gln Ala Glu Phe Pro Leu Gly Pro Val Thr Thr Ala His
    50                  55                  60

Arg Gly Thr Tyr Arg Cys Phe Gly Ser Tyr Asn Asn His Ala Trp Ser
65                  70                  75                  80

Phe Pro Ser Glu Pro Val Lys Leu Leu Val Thr Gly Asp Ile Glu Asn
                85                  90                  95

Thr Ser Leu Ala Pro Glu Asp Pro Thr Phe Pro Asp His Ala Leu Trp
            100                 105                 110

Asp His Thr Ala Gln
        115

<210> SEQ ID NO 49
<211> LENGTH: 142
<212> TYPE: PRT
<213> ORGANISM: Artificial
<220> FEATURE:
<223> OTHER INFORMATION: Synthetic peptide

<400> SEQUENCE: 49

Leu Lys Leu Val Val Thr Gly Leu Tyr Asp Thr Pro Asn Leu Trp Val
1               5                   10                  15

Tyr Pro Arg Pro Glu Val Thr Leu Gly Glu Asn Val Thr Phe Phe Cys

```
                    20                  25                  30

Gln Leu Lys Thr Ala Thr Ser Lys Phe Phe Leu Lys Glu Arg Gly
         35                  40                  45

Ser Asn His Ile Gln Asn Lys Tyr Gly Asn Ile Gln Ala Glu Phe Pro
     50                  55                  60

Met Gly Pro Val Thr Arg Ala His Arg Gly Thr Tyr Arg Cys Phe Gly
 65              70                  75                  80

Ser Tyr Asn Asp Tyr Ala Trp Ser Phe Pro Ser Glu Pro Val Thr Leu
                 85                  90                  95

Leu Ile Thr Gly Gly Val Glu Asn Ser Ser Leu Ala Pro Thr Asp Pro
                100                 105                 110

Thr Ser Ser Leu Asp Tyr Trp Glu Phe Asp Leu Ser Thr Asn Glu Ser
        115                 120                 125

Gly Leu Gln Lys Asp Ser Ala Phe Trp Asp His Thr Thr Gln
        130                 135                 140

<210> SEQ ID NO 50
<211> LENGTH: 134
<212> TYPE: PRT
<213> ORGANISM: Artificial
<220> FEATURE:
<223> OTHER INFORMATION: Synthetic peptide

<400> SEQUENCE: 50

Tyr Asp Thr Pro Asn Leu Trp Val Tyr Pro Gln Pro Glu Val Thr Leu
  1               5                  10                  15

Gly Glu Asn Val Thr Phe Phe Cys Gln Leu Lys Thr Ala Thr Ser Lys
                 20                  25                  30

Phe Phe Leu Leu Lys Glu Arg Gly Ser Asn His Ile Gln Asn Lys Tyr
         35                  40                  45

Gly Asn Ile Gln Ala Glu Phe Pro Met Gly Pro Val Thr Arg Ala His
     50                  55                  60

Arg Gly Thr Tyr Arg Cys Phe Gly Ser Tyr Asn Asp Tyr Ala Trp Ser
 65              70                  75                  80

Phe Pro Ser Glu Pro Val Thr Leu Leu Ile Thr Gly Gly Val Glu Asn
                 85                  90                  95

Ser Ser Leu Ala Pro Thr Asp Pro Thr Ser Ser Leu Asp Tyr Trp Glu
                100                 105                 110

Phe Asp Leu Ser Thr Asn Glu Ser Gly Leu Gln Lys Asp Ser Ala Phe
        115                 120                 125

Trp Asp His Thr Thr Gln
        130

<210> SEQ ID NO 51
<211> LENGTH: 110
<212> TYPE: PRT
<213> ORGANISM: Artificial
<220> FEATURE:
<223> OTHER INFORMATION: Synthetic peptide

<400> SEQUENCE: 51

Gln Ser Lys Ala Gln Val Leu Gln Ser Val Ala Gly Gln Thr Leu Thr
  1               5                  10                  15

Val Arg Cys Gln Tyr Pro Pro Thr Gly Ser Leu Tyr Glu Lys Lys Gly
                 20                  25                  30

Trp Cys Lys Glu Ala Ser Ala Leu Val Cys Ile Arg Leu Val Thr Ser
         35                  40                  45
```

```
Ser Lys Pro Arg Thr Val Ala Trp Thr Ser Arg Phe Thr Ile Trp Asp
    50                  55                  60

Asp Pro Asp Ala Gly Phe Phe Thr Val Thr Met Thr Asp Leu Arg Glu
 65                  70                  75                  80

Glu Asp Ser Gly His Tyr Trp Cys Arg Ile Tyr Arg Pro Ser Asp Asn
                 85                  90                  95

Ser Val Ser Lys Ser Val Arg Phe Tyr Leu Val Val Ser Pro
                100                 105                 110

<210> SEQ ID NO 52
<211> LENGTH: 302
<212> TYPE: PRT
<213> ORGANISM: Artificial
<220> FEATURE:
<223> OTHER INFORMATION: Synthetic peptide

<400> SEQUENCE: 52

Met Ser Ser Thr Leu Pro Ala Leu Leu Cys Val Gly Leu Cys Leu Ser
  1               5                  10                  15

Gln Arg Ile Ser Ala Gln Gln Thr Leu Pro Lys Pro Phe Ile Trp
                 20                  25                  30

Ala Glu Pro His Phe Met Val Pro Lys Glu Lys Gln Val Thr Ile Cys
                 35                  40                  45

Cys Gln Gly Asn Tyr Gly Ala Val Glu Tyr Gln Leu His Phe Glu Gly
 50                  55                  60

Ser Leu Phe Ala Val Asp Arg Pro Lys Pro Pro Glu Arg Ile Asn Lys
 65                  70                  75                  80

Val Lys Phe Tyr Ile Pro Asp Met Asn Ser Arg Met Ala Gly Gln Tyr
                 85                  90                  95

Ser Cys Ile Tyr Arg Val Gly Glu Leu Trp Ser Glu Pro Ser Asn Leu
                100                 105                 110

Leu Asp Leu Val Val Thr Glu Met Tyr Asp Thr Pro Thr Leu Ser Val
            115                 120                 125

His Pro Gly Pro Glu Val Ile Ser Gly Glu Lys Val Thr Phe Tyr Cys
130                 135                 140

Arg Leu Asp Thr Ala Thr Ser Met Phe Leu Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Gly Ser
                180                 185                 190

Tyr Asn Asn His Ala Trp Ser Phe Pro Ser Glu Pro Val Lys Leu Leu
            195                 200                 205

Val Thr Gly Asp Ile Glu Asn Thr Ser Leu Ala Pro Glu Asp Pro Thr
210                 215                 220

Phe Pro Ala Asp Thr Trp Gly Thr Tyr Leu Leu Thr Thr Glu Thr Gly
225                 230                 235                 240

Leu Gln Lys Asp His Ala Leu Trp Asp His Thr Ala Gln Asn Leu Leu
                245                 250                 255

Arg Met Gly Leu Ala Phe Leu Val Leu Val Ala Leu Val Trp Phe Leu
            260                 265                 270

Val Glu Asp Trp Leu Ser Arg Lys Arg Thr Arg Glu Arg Ala Ser Arg
            275                 280                 285

Ala Thr Trp Glu Gly Arg Arg Arg Leu Asn Thr Gln Thr Leu
        290                 295                 300
```

```
<210> SEQ ID NO 53
<211> LENGTH: 393
<212> TYPE: PRT
<213> ORGANISM: Artificial
<220> FEATURE:
<223> OTHER INFORMATION: Synthetic peptide

<400> SEQUENCE: 53

Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
            20                  25                  30

Asp Thr Pro Thr Leu Ser Val His Pro Gly Pro Glu Val Ile Ser Gly
        35                  40                  45

Glu Lys Val Thr Phe Tyr Cys Arg Leu Asp Thr Ala Thr Ser Met Phe
    50                  55                  60

Leu Leu Leu Lys Glu Gly Arg Ser Ser His Val Gln Arg Gly Tyr Gly
65                  70                  75                  80

Lys Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
            100                 105                 110

Pro Ser Glu Pro Val Lys Leu Leu Val Thr Gly Asp Ile Glu Asn Thr
        115                 120                 125

Ser Leu Ala Pro Glu Asp Pro Thr Phe Pro Asp Thr Trp Gly Thr Tyr
    130                 135                 140

Leu Leu Thr Thr Glu Thr Gly Leu Gln Lys Asp His Ala Leu Trp Asp
145                 150                 155                 160

Pro Glu Pro Lys Ser Ser Asp Lys Thr His Thr Cys Pro Pro Cys Pro
                165                 170                 175

Ala Pro Glu Phe Glu Gly Ala Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
    210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
            260                 265                 270

Ala Leu Pro Ala Pro Ile Glu Lys Thr Ile Ser Lys Ala Lys Gly Gln
        275                 280                 285

Pro Arg Glu Pro Gln Val Tyr Thr Leu Pro Pro Ser Arg Asp Glu Leu
    290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
            340                 345                 350

Tyr Ser Lys Leu Thr Val Asp Lys Ser Arg Trp Gln Gln Gly Asn Val
        355                 360                 365
```

Phe Ser Cys Ser Val Met His Glu Ala Leu His Asn His Tyr Thr Gln
370                 375                 380

Lys Ser Leu Ser Leu Ser Pro Gly Lys
385                 390

<210> SEQ ID NO 54
<211> LENGTH: 393
<212> TYPE: PRT
<213> ORGANISM: Artificial
<220> FEATURE:
<223> OTHER INFORMATION: Synthetic peptide

<400> SEQUENCE: 54

Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
                20                  25                  30

Asp Thr Pro Thr Leu Ser Val His Pro Gly Pro Glu Val Ile Ser Gly
            35                  40                  45

Glu Lys Val Thr Phe Tyr Cys Arg Leu Asp Thr Ala Thr Ser Met Phe
50                  55                  60

Leu Leu Leu Gln Glu Gly Gln Ser Ser Gln Val Gln Gln Gly Tyr Gly
65                  70                  75                  80

Lys Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
            100                 105                 110

Pro Ser Glu Pro Val Lys Leu Leu Val Thr Gly Asp Ile Glu Asn Thr
        115                 120                 125

Ser Leu Ala Pro Glu Asp Pro Thr Phe Pro Asp Thr Trp Gly Thr Tyr
130                 135                 140

Leu Leu Thr Thr Glu Thr Gly Leu Gln Lys Asp His Ala Leu Trp Asp
145                 150                 155                 160

Pro Glu Pro Lys Ser Ser Asp Lys Thr His Thr Cys Pro Pro Cys Pro
                165                 170                 175

Ala Pro Glu Phe Glu Gly Ala Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
            260                 265                 270

Ala Leu Pro Ala Pro Ile Glu Lys Thr Ile Ser Lys Ala Lys Gly Gln
        275                 280                 285

Pro Arg Glu Pro Gln Val Tyr Thr Leu Pro Pro Ser Arg Asp Glu Leu
290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

```
Tyr Lys Thr Thr Pro Pro Val Leu Asp Ser Asp Gly Ser Phe Phe Leu
            340                 345                 350

Tyr Ser Lys Leu Thr Val Asp Lys Ser Arg Trp Gln Gln Gly Asn Val
        355                 360                 365

Phe Ser Cys Ser Val Met His Glu Ala Leu His Asn His Tyr Thr Gln
370                 375                 380

Lys Ser Leu Ser Leu Ser Pro Gly Lys
385                 390

<210> SEQ ID NO 55
<211> LENGTH: 15
<212> TYPE: PRT
<213> ORGANISM: Artificial
<220> FEATURE:
<223> OTHER INFORMATION: Synthetic peptide

<400> SEQUENCE: 55

Thr Phe Tyr Cys Arg Leu Asp Thr Ala Thr Ser Met Phe Leu Leu
1               5                   10                  15

<210> SEQ ID NO 56
<211> LENGTH: 15
<212> TYPE: PRT
<213> ORGANISM: Artificial
<220> FEATURE:
<223> OTHER INFORMATION: Synthetic peptide

<400> SEQUENCE: 56

Thr Phe Phe Cys Gln Leu Lys Thr Ala Thr Ser Lys Phe Phe Leu
1               5                   10                  15

<210> SEQ ID NO 57
<211> LENGTH: 10
<212> TYPE: PRT
<213> ORGANISM: Artificial
<220> FEATURE:
<223> OTHER INFORMATION: Synthetic peptide

<400> SEQUENCE: 57

Leu Asp Thr Ala Thr Ser Met Phe Leu Leu
1               5                   10

<210> SEQ ID NO 58
<211> LENGTH: 10
<212> TYPE: PRT
<213> ORGANISM: Artificial
<220> FEATURE:
<223> OTHER INFORMATION: Synthetic peptide

<400> SEQUENCE: 58

Leu Lys Thr Ala Thr Ser Lys Phe Phe Leu
1               5                   10

<210> SEQ ID NO 59
<211> LENGTH: 10
<212> TYPE: PRT
<213> ORGANISM: Artificial
<220> FEATURE:
<223> OTHER INFORMATION: Synthetic peptide

<400> SEQUENCE: 59

Val Cys Ile Arg Leu Val Thr Ser Ser Lys
1               5                   10

<210> SEQ ID NO 60
```

```
<211> LENGTH: 10
<212> TYPE: PRT
<213> ORGANISM: Artificial
<220> FEATURE:
<223> OTHER INFORMATION: Synthetic peptide
<220> FEATURE:
<221> NAME/KEY: Hydrophobic_amino_acid
<222> LOCATION: (9)..(9)
<223> OTHER INFORMATION: Xaa=Hydrophobic amino acid

<400> SEQUENCE: 60

Val Thr Ser Ser Lys Pro Arg Thr Xaa Ala
1               5                   10

<210> SEQ ID NO 61
<211> LENGTH: 15
<212> TYPE: PRT
<213> ORGANISM: Artificial
<220> FEATURE:
<223> OTHER INFORMATION: Synthetic amino acid
<220> FEATURE:
<221> NAME/KEY: Hydrophobic_amino_acid
<222> LOCATION: (14)..(14)
<223> OTHER INFORMATION: Xaa=Hydrophobic_amino_acid

<400> SEQUENCE: 61

Val Cys Ile Arg Leu Val Thr Ser Ser Lys Pro Arg Thr Xaa Ala
1               5                   10                  15
```